US011280785B2

(12) United States Patent
Reinhartz et al.

(10) Patent No.: US 11,280,785 B2
(45) Date of Patent: *Mar. 22, 2022

(54) LIQUID-TRANSFER DEVICE PARTICULARLY USEFUL AS A CAPTURING DEVICE IN A BIOLOGICAL ASSAY PROCESS

(71) Applicant: RealBio Technologies Ltd., Kfar-HaNagid (IL)

(72) Inventors: Avraham Reinhartz, Gan-Yavne (IL); Sara Alajem, Kfar-Hanagid (IL)

(73) Assignee: RealBio Technologies Ltd., Kfar-HaNagid (IL)

( * ) Notice: Subject to any disclaimer, the term of this patent is extended or adjusted under 35 U.S.C. 154(b) by 340 days.

This patent is subject to a terminal disclaimer.

(21) Appl. No.: 15/954,309

(22) Filed: Apr. 16, 2018

(65) Prior Publication Data

US 2018/0231543 A1 Aug. 16, 2018

Related U.S. Application Data

(62) Division of application No. 12/999,408, filed as application No. PCT/IL2009/000643 on Jun. 29, 2009, now Pat. No. 9,952,211.

(Continued)

(51) Int. Cl.
*G01N 33/543* (2006.01)
*G01N 33/558* (2006.01)
*B01L 3/00* (2006.01)

(52) U.S. Cl.
CPC ...... *G01N 33/54386* (2013.01); *B01L 3/5023* (2013.01); *G01N 33/558* (2013.01);
(Continued)

(58) Field of Classification Search
CPC .............. G01N 33/558; G01N 33/54386
See application file for complete search history.

(56) References Cited

U.S. PATENT DOCUMENTS

| 3,791,932 A | 2/1974 | Schuurs et al. |
| 3,839,153 A | 10/1974 | Schuurs et al. |

(Continued)

FOREIGN PATENT DOCUMENTS

| DE | 19822770 A1 | 11/1999 |
| EP | 284232 A1 | 9/1988 |

(Continued)

OTHER PUBLICATIONS

International Search Report and Written Opinion in PCT/US2012/055676, dated Jan. 2, 2013.

(Continued)

*Primary Examiner* — Rebecca M Giere
*Assistant Examiner* — Xiaoyan Zou
(74) *Attorney, Agent, or Firm* — Jones Robb, PLLC

(57) ABSTRACT

A device and method for use in capturing a substance in a liquid, by feeding the liquid through a capturing device including: a lateral capillary flow matrix and a capturing matrix in fluid communication with the lateral capillary flow matrix so as to produce two lateral flows sufficient to impart transverse oscillations to the lateral flow in the capturing matrix, such oscillations driving the liquid into the interior of the capturing matrix thereby exposing its interior to the liquid.

31 Claims, 15 Drawing Sheets

Related U.S. Application Data

(60) Provisional application No. 61/076,650, filed on Jun. 29, 2008.

(52) U.S. Cl.
CPC . *B01L 2300/069* (2013.01); *B01L 2300/0825* (2013.01); *B01L 2300/0887* (2013.01); *B01L 2300/161* (2013.01); *B01L 2400/0406* (2013.01)

(56) References Cited

U.S. PATENT DOCUMENTS

| | | | |
|---|---|---|---|
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,362,901 A | 12/1982 | Nigol et al. | |
| 4,623,461 A | 11/1986 | Hossom et al. | |
| 4,666,828 A | 5/1987 | Gusella | |
| 4,683,202 A | 7/1987 | Mullis | |
| 4,801,531 A | 1/1989 | Frossard | |
| 4,818,677 A | 4/1989 | Hay-Kaufman et al. | |
| 4,833,087 A | 5/1989 | Hinckley | |
| 4,855,240 A | 8/1989 | Rosenstein et al. | |
| 4,857,453 A * | 8/1989 | Ullman | G01N 33/54366 435/7.92 |
| 4,861,711 A | 8/1989 | Friesen et al. | |
| 4,879,219 A | 11/1989 | Wands et al. | |
| 4,912,034 A | 3/1990 | Kalra et al. | |
| 4,943,522 A | 7/1990 | Eisinger et al. | |
| 4,956,302 A | 9/1990 | Gordon et al. | |
| 4,960,691 A | 10/1990 | Gordon et al. | |
| 4,981,786 A | 1/1991 | Dafforn et al. | |
| 5,011,771 A | 4/1991 | Bellet et al. | |
| 5,081,017 A | 1/1992 | Longoria | |
| 5,089,389 A | 2/1992 | Pelanek et al. | |
| 5,120,643 A | 6/1992 | Ching et al. | |
| 5,192,659 A | 3/1993 | Simons | |
| 5,198,193 A | 3/1993 | Bunce et al. | |
| 5,202,268 A | 4/1993 | Kuhn et al. | |
| 5,223,220 A | 6/1993 | Fan et al. | |
| 5,252,496 A | 10/1993 | Kang et al. | |
| 5,272,057 A | 12/1993 | Smulson et al. | |
| 5,281,521 A | 1/1994 | Trojanowski et al. | |
| 5,384,264 A * | 1/1995 | Chen | B01L 3/5023 422/400 |
| 5,772,961 A | 6/1998 | Mico | |
| 5,783,401 A | 7/1998 | Toledano | |
| 5,821,073 A | 10/1998 | Lee | |
| 5,853,670 A | 12/1998 | Bunce | |
| 5,885,526 A | 3/1999 | Chu | |
| 5,916,521 A | 6/1999 | Bunce et al. | |
| 6,008,056 A | 12/1999 | Thieme | |
| 6,156,270 A | 12/2000 | Buechler | |
| 6,197,598 B1 | 3/2001 | Schrier et al. | |
| 6,231,815 B1 | 5/2001 | Bainczyk et al. | |
| 6,297,020 B1 | 10/2001 | Brock | |
| 6,432,358 B2 | 8/2002 | Norris et al. | |
| 6,464,939 B1 | 10/2002 | Bachand et al. | |
| 6,485,982 B1 | 11/2002 | Charlton | |
| 6,566,051 B1 | 5/2003 | Owens | |
| 6,634,243 B1 | 10/2003 | Wickstead et al. | |
| 6,767,710 B2 | 7/2004 | DiNello et al. | |
| 6,811,753 B2 | 11/2004 | Hirao et al. | |
| 6,812,038 B1 | 11/2004 | Mendel-Hartvig et al. | |
| 6,818,452 B2 | 11/2004 | Wong | |
| 6,890,484 B2 | 5/2005 | Bautista et al. | |
| 7,141,212 B2 | 11/2006 | Catt et al. | |
| 7,189,522 B2 | 3/2007 | Esfandiari | |
| 7,205,159 B2 | 4/2007 | Cole et al. | |
| 7,256,053 B2 | 8/2007 | Hu | |
| 7,387,890 B2 | 6/2008 | Esfandiari | |
| 7,476,533 B2 | 1/2009 | Meathrel et al. | |
| 7,549,492 B2 | 6/2009 | Pond | |
| 7,595,196 B2 | 9/2009 | Guo et al. | |
| 7,682,833 B2 | 3/2010 | Miller et al. | |
| 7,785,865 B2 | 8/2010 | Qinwei | |
| 8,465,696 B2 | 6/2013 | Huffstodt et al. | |
| 8,507,260 B2 | 8/2013 | Alajem et al. | |
| 8,557,600 B2 | 10/2013 | Mabuchi et al. | |
| 9,101,927 B2 | 8/2015 | Alajem et al. | |
| 9,726,581 B2 | 8/2017 | Gargir et al. | |
| 9,952,211 B2 * | 4/2018 | Reinhartz | G01N 33/54386 |
| 10,335,783 B2 | 7/2019 | Alajem et al. | |
| 10,598,572 B2 | 3/2020 | Gargir et al. | |
| 2001/0005488 A1 | 6/2001 | Hirao et al. | |
| 2001/0048893 A1 | 12/2001 | Norris et al. | |
| 2002/0085958 A1 | 7/2002 | Nemcek et al. | |
| 2002/0173050 A1 | 11/2002 | DiNello et al. | |
| 2003/0044317 A1 | 3/2003 | Catt et al. | |
| 2003/0068646 A1 | 4/2003 | Singh et al. | |
| 2003/0129767 A1 | 7/2003 | Bautista et al. | |
| 2003/0138353 A1 | 7/2003 | Bargoot et al. | |
| 2003/0171698 A1 | 9/2003 | Rubin et al. | |
| 2004/0015101 A1 | 1/2004 | Rubin et al. | |
| 2004/0045891 A1 | 3/2004 | Gilbert et al. | |
| 2004/0082077 A1 | 4/2004 | Hu | |
| 2004/0092036 A1 * | 5/2004 | Chen | G01N 33/54353 436/514 |
| 2004/0115831 A1 | 6/2004 | Meathrel et al. | |
| 2004/0219690 A1 | 11/2004 | Choi et al. | |
| 2005/0079629 A1 | 4/2005 | Guo et al. | |
| 2005/0124077 A1 | 6/2005 | Cole et al. | |
| 2006/0133956 A1 | 6/2006 | Hamanaka | |
| 2006/0134803 A1 | 6/2006 | Esfandiari | |
| 2006/0160078 A1 | 7/2006 | Cardy et al. | |
| 2006/0292700 A1 | 12/2006 | Wang et al. | |
| 2007/0039835 A1 | 2/2007 | Rossier et al. | |
| 2007/0243628 A1 | 10/2007 | Mabuchi et al. | |
| 2008/0112848 A1 | 5/2008 | Huffstodt et al. | |
| 2008/0145835 A1 | 6/2008 | Alajem et al. | |
| 2008/0213133 A1 | 9/2008 | Wallace et al. | |
| 2010/0099112 A1 * | 4/2010 | Zhou | G01N 33/558 435/7.1 |
| 2010/0239459 A1 | 9/2010 | Alajem et al. | |
| 2011/0189792 A1 | 8/2011 | Reinhartz et al. | |
| 2014/0248389 A1 | 9/2014 | Alajem et al. | |
| 2014/0339090 A1 | 11/2014 | Huang et al. | |
| 2016/0038935 A1 | 2/2016 | Alajem et al. | |
| 2018/0045620 A1 | 2/2018 | Gargir et al. | |
| 2019/0001332 A1 | 1/2019 | Ben Asouli et al. | |

FOREIGN PATENT DOCUMENTS

| | | |
|---|---|---|
| EP | 1236514 A2 | 9/2002 |
| EP | 1044372 B1 | 9/2003 |
| WO | 9405426 A1 | 3/1994 |
| WO | 9517965 A1 | 7/1995 |
| WO | 9519845 A2 | 7/1995 |
| WO | 1999/034190 A1 | 7/1997 |
| WO | 1999036776 A1 | 7/1999 |
| WO | 0062060 | 10/2000 |
| WO | 0129558 A1 | 4/2001 |
| WO | 2001027626 A2 | 4/2001 |
| WO | 2002006830 A1 | 1/2002 |
| WO | 2005031355 A1 | 4/2005 |
| WO | 2006062312 A1 | 6/2006 |
| WO | 2006080021 A2 | 8/2006 |
| WO | 2006087697 A2 | 8/2006 |
| WO | 2008018073 A1 | 2/2008 |
| WO | 2009152373 A1 | 12/2009 |
| WO | 2010007613 A1 | 1/2010 |

(56) References Cited

FOREIGN PATENT DOCUMENTS

| WO | 2013095729 A1 | 6/2013 |
|----|---------------|--------|
| WO | 2017109775 A1 | 6/2017 |

OTHER PUBLICATIONS

"Diagnostic Components", www.schleicher-schuell.com/bioscience, 26 pages.
Akinh-Kocak, Sedef "The Influence of Fiber Swelling on Paper Wetting", The Graduate School, The University of Maine, Aug. 2001. (144 pages).
Whatman, "Components for Diagnostic Kit Developers, Solutions for Everyday Problems", www.whatman.com, Jan. 2007. (32 pages).
Extended Search Report in EP Appln No. 15195010.2, dated Mar. 17, 2016.
Extended Search Report in EP Appln No. 06701713.7, dated Sep. 24, 2010, (8 pages total).
Jones, et al. "Effects of Adhesive Migration in Lateral Flow Assays", IVD Technology, 2000, (8 pages total).
Jallerat et al. "Filter Membranes and Bioseparation Equipment and Supplies", IVD Technology 2002, (4 pages total).
Millipore Corporation Product Literature, "Rapid Lateral Flow Test Strips", May 2008, (42 pages total).
International Preliminary Report on Patentability in PCT/IL2006/000121, dated Oct. 12, 2007.
International Search Report in PCT/IL2006/000121, dated Oct. 12, 2007.
Written Opinion in PCT/IL2006/000121, dated Sep. 24, 2010, (8 pages total).
International Preliminary Report on Patentability in PCT/IL2009/000643, dated Jan. 5, 2011.
Written Opinion in PCT/IL2009/000643, dated Dec. 29, 2010.
International Search Report in PCT/IL2009/000643, dated Nov. 24, 2009.
Final Office Action in U.S. Appl. No. 12/999,408, dated Jan. 29, 2016.
Non-Final Office Action in U.S. Appl. No. 12/999,408, dated Sep. 13, 2016.
Final Office Action in U.S. Appl. No. 12/999,408, dated Mar. 7, 2017.
Notice of Allowance in U.S. Appl. No. 12/999,408, dated Dec. 18, 2017.
Non-Final Office Action in U.S. Appl. No. 12/999,408, dated Jul. 17, 2015.
Final Office Action in U.S. Appl. No. 12/999,408, dated Oct. 9, 2013.
Non-Final Office Action in U.S. Appl. No. 12/999,408, dated Apr. 8, 2013.
Communication dated Sep. 25, 2017, received from the European Patent Office in European Application No. 09787449.9 (6 pages).
Communication dated Jul. 18, 2016, received from the European Patent Office in European Application No. 09787449.9 (5 pages).
Communication dated Jun. 5, 2014, received from the European Patent Office in European Application No. 09787449.9 (5 pages).
Communication dated July 9, 2018, received from the European Patent Office in European Application No. 09787449.9 (4 pages).
Summons to Attend Oral Proceedings issued in corresponding European Application No. 09787449.9, dated Oct. 23, 2019, (6 pages total).
EP09787449 Communication—dated Aug. 24, 2020.
EP09787449 Communication—dated Aug. 27, 2020.
EP09787449 Communication—Text for Grant—dated Nov. 3, 2020.
EP09787449 Communication—Intent to Grant Patent—dated Nov. 3, 2020.

* cited by examiner

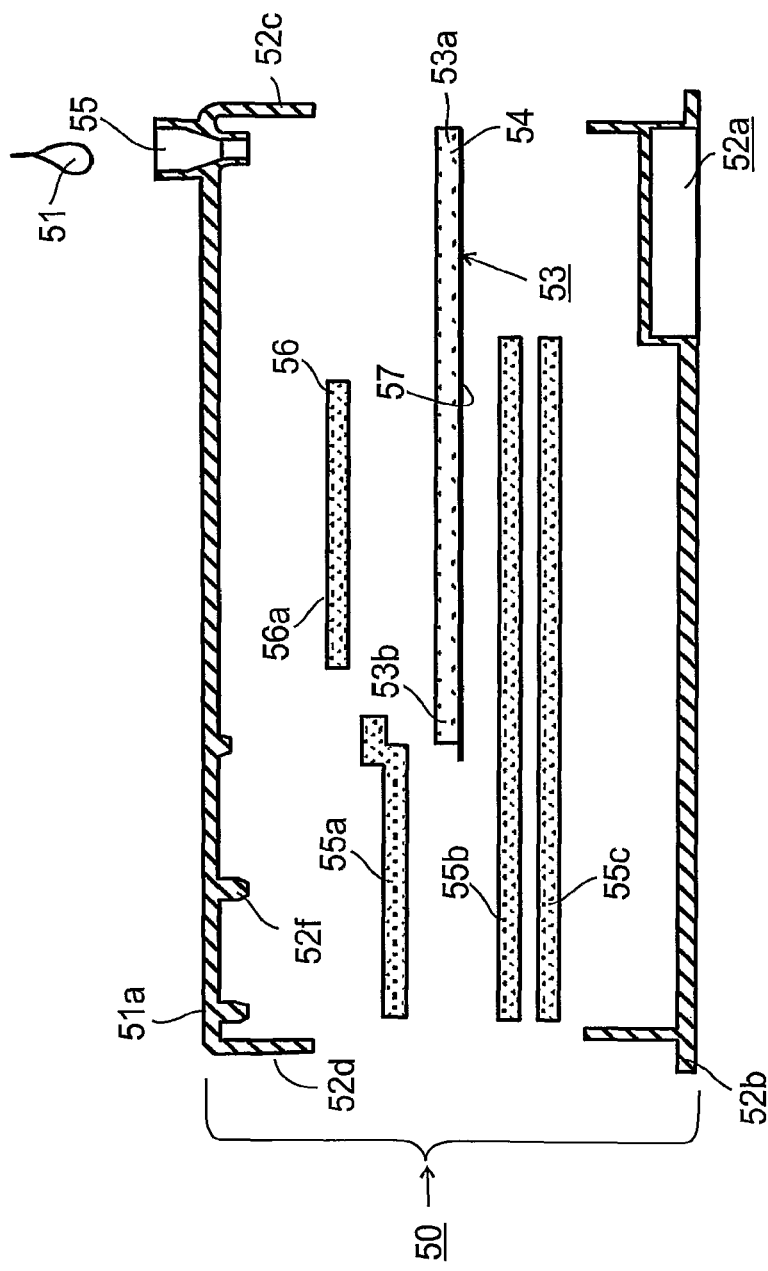
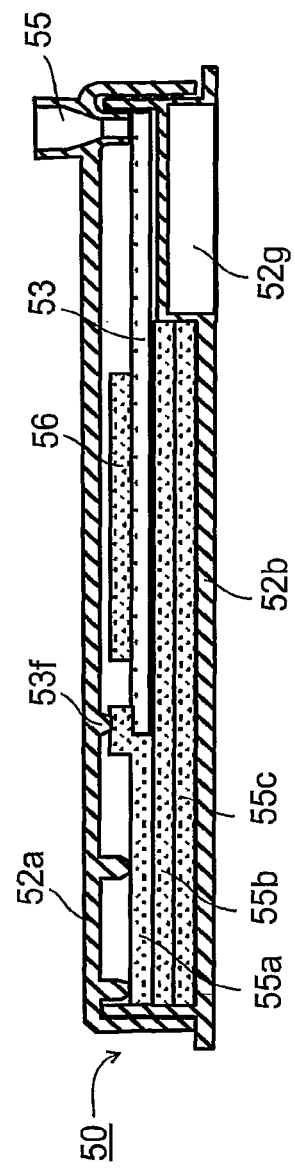
FIG. 5A
FIG. 5B

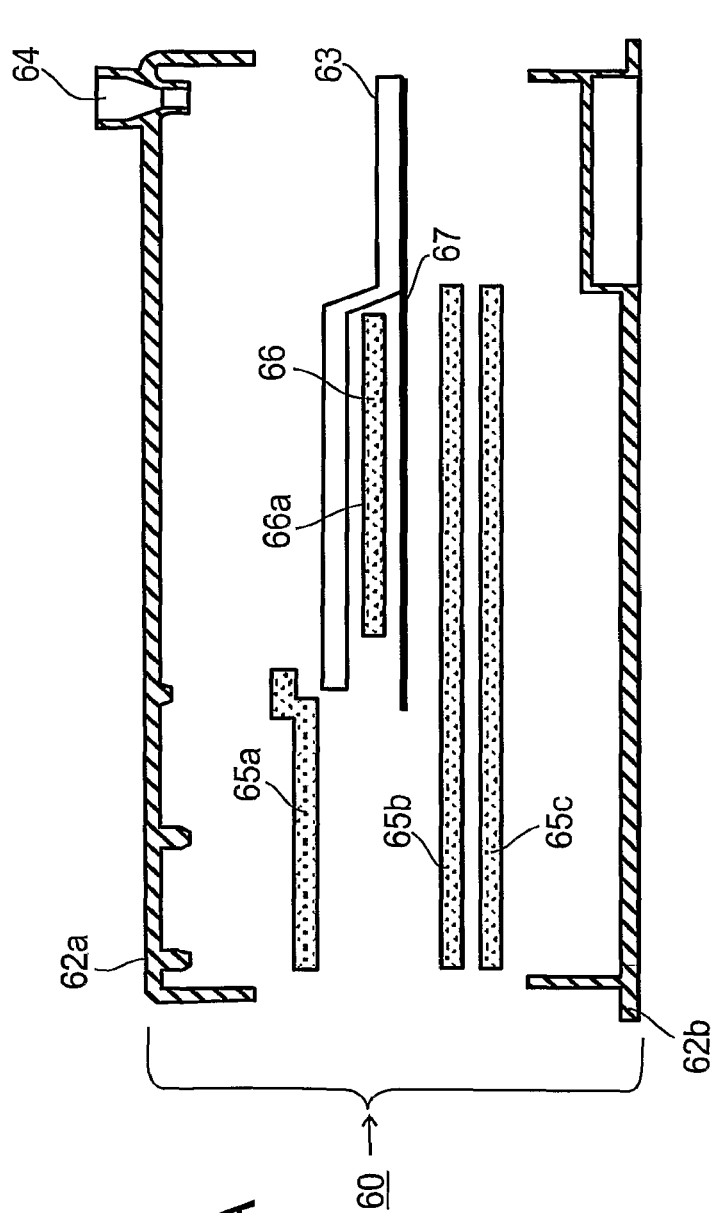
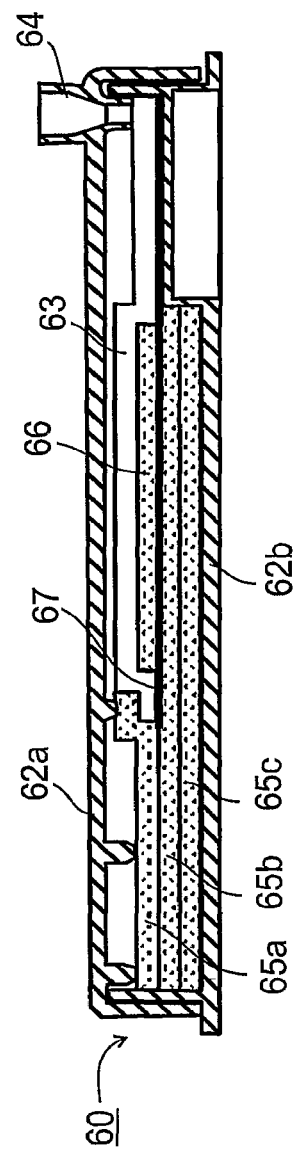
FIG. 6A
FIG. 6B

LIQUID-TRANSFER DEVICE PARTICULARLY USEFUL AS A CAPTURING DEVICE IN A BIOLOGICAL ASSAY PROCESS

RELATED APPLICATION

This application is a divisional of U.S. patent application Ser. No. 12/999,408, filed Mar. 17, 2011 (now U.S. Pat. No. 9,952,211), which is a National Stage application of International Application No. PCT/IL2009/000643, filed Jun. 29, 2009, which claims the benefit of U.S. Provisional Application No. 61/076,650, filed Jun. 29, 2008 (now expired), each of which are incorporated herein by reference.

FIELD AND BACKGROUND OF THE INVENTION

The present invention relates to a liquid-transfer device particularly useful as a capturing device for capturing substances in a liquid. The invention is especially useful in biological assay devices, wherein the substance in the liquid is a biological substance to be immobilized and captured for analysis purposes, or for reaction with another substance contained within another liquid.

The invention is described below with respect to devices and methods for performing accelerated analytic and synthetic analyses procedures, such as those relating immunological, genetic, biochemical and bioanalytical processes and biochemical assays. Such assays may be performed for a variety of purposes including, but not limited to, isolation and/or detection of proteins or polynucleotides, detection of blood group antigens and their antibodies, screening of drug candidate and compounds, life science research and clinical and molecular diagnostics.

Recent developments in a variety of research and diagnostic fields have created a need for improved and ari-Plerated methods and apparatus for performing analytical, particularly, bioanalytical procedures and assays, to increase research efficiency and saving costs. Such need exists mainly in solid phase reactions which are time consuming processes.

Over the years, numerous biochemical processes were designed to be performed on different types of solid phase reactions including, biochemical processes, including synthesis, separation and extraction processes, diagnostic processes, and the like.

These biochemical processes were designed to be performed on different types of solid phase matrixes. Solid phase matrixes may by of non-water permeable material such as glass or polystyrene, which may be in form of tubes, microtitration plates, or microscopic slides. The solid phase may be comprised of a bibulous or porous membrane such as nylon or nitrocellulose or glass fibers and the like.

Biochemical reactions are driven by reactant collisions which are effected by energy kinetics of the reactants and their concentration. (The collision theory). "*The physical basis of biochemistry: the foundations of molecular biophysics* By Peter R. Bergethon, Edition: Published by Springer, 1998.

In typical biochemical solid phase reactions such as immunoassay reactions, at feast two types of reactants are involved. One type of reactant is immobilized to the solid phase (antibody or antigen), and other reactant, having binding affinity to the immobilized reactant, is free in the reaction solution. Reactant immobilization therefore reduces energy kinetics and collision frequency, and therefore prolongs reaction time. "*ELISA and other solid phase immunoassays: theoretical and practical aspects* By D. M. Kemeny, Stephen J. Challacombe, Edition: illustrated, Published by John Wiley and Sons, 1988."

In order to accelerate solid phase reactions, two type of solution were used. One type was a flow-through type of assay, in particular immunoassays type such as described in Valkirs et. al., U.S. Pat. No. 4,632,901. This patent disclose a device containing a porous binding membrane as a solid phase matrix to which receptor molecule are bound, and in which the binding membrane is in contact with an absorbent membrane. A heterogeneous reaction is effected in a short time, while a sample containing an analyte is applied on top of the binding membrane, followed by washing solutions and signal producing liquid.

A different type of flow through device was disclosed by Mabuchi et. al, U.S. Pat. Application Publication 2007/0243628, relating to a device for detection of proteins on a blotted membrane. The device comprises several layers including a support layer placed below the blotting membrane, and a flow distributor layer placed above the blotting membrane. The layers are held by a plastic housing having a reservoir for holding the reagents above the flow distributor.

The reaction liquids are transferred through the layers by vacuum or positive gas pressure. Such methods therein described are rapid, but flow control is difficult and the results will have low reproducibility.

A different approach to accelerate biochemical immunoassays is the use of lateral flow devices, sometimes also named as immuno-chromatography devices. Gordon et. al., U.S. Pat. No. 4,956,302 discloses such a device for the detection of antigens or antibodies in a fluid sample by lateral flow through a bibulous membrane strip enclosed in a plastic housing.

Another device is described by Bunce et. al. U.S. Pat. No. 5,198,193, which reduces the problem of formation of undesirable complexes produces by the close presence of samples and reagents in a dense porous material. The device comprises two liquid flow channels leading to a common site and operable to deliver liquid to this site in a sequentially timed manner following simultaneous application of such liquid to the channels. A capture zone is positioned in the common site or downstream of it.

Another dual path immunoassay device is disclosed by Esfandiari U.S. Pat. No. 7,189,522 intended to overcome interactions between sample and reaction reactants such as conjugates which lead to aggregation. The solution described in that patent was (a) to separate the flow of the sample from the flow of the conjugate by using two distinct flow paths, two inlets each in every path, and (b) to control the timing of the two flows so that at a particular time, only one flow is taking place in the capture zone. The device described is composed of two flow path perpendicular to each other. The two paths have portions which overlie one another and the capture zone is immobilized on one or both of the flow path material at the junction. The device is operated by applying the sample to one path, usually that having a higher pore size.

Such solutions do not solve the main problem in lateral flow, which is the contradiction between the requirement for rapid assay and high sensitivity. Rapid assay is achieved by fast lateral flow, due to high wicking property of the membrane, in Nitrocellulose membranes the wicking property is effected by pore size, Membranes of 5 micrometer have wicking rate of nearly 200 s/4 cm, as membranes of 15 micrometer have higher rate, around 70 s/4 cm. High sensitivity is obtained by high membrane binding capacity, lower pore size increase binding capacity, for example, in 0.1 μm Nitrocellulose membranes the protein binding capacity is 100-150 μg IgG/cm$^2$ as for 0.45 μm membranes the binding capacity is 50-100 μg IgG/cm$^2$.

Buechler et. al., U.S. Pat. No. 6,156,270, describes a system and a device for lateral flow immunoassay using a non bibulous, non porous, flow path. The device comprises two opposing surfaces disposed at a capillary distance apart. One of the sides has a capture zone in which receptor molecules are immobilized.

Eisinger et. al. U.S. Pat. No. 4,943,522 describes a lateral flow device having a non-bibulous membrane for conducting an immunoassay.

U.S. Pat. No. 5,202,268 teaches a multi-layered test card for the determination of substances in liquids wherein the liquids flow from a first membrane into a second membrane and back to the first membrane. In order to enable such unipath flow, each membrane is divided by liquid flow barriers in order to disattach the intimate contact between the membranes. This configuration prevents parallel flow and enables a sequential flow through the membranes.

A complex formed by a specific binding reaction is generally not directly observable. Various techniques have been devised for labeling one member of the specific binding pair to enable visualization and measurement of the complex. Known labels include radioactivity, gold particles, magnetic particles, chromophores, fluorophores and enzymes. When a member of a specific binding pair is conjugated to an enzyme, the complex may be detected by the enzymatic activation of a reaction system including a signal generating substrate/cofactor group wherein a compound, such as a dyestuff, is activated to produce a detectable signal.

One approach for increasing speed, and simplifying such binding assays performed on a solid phase matrix, utilizes a one step lateral flow capillary device such as depicted in FIG. 1, to be described below. Such choices are extremely useful as they are simple to operate even by an unskilled person, or under non-laboratory conditions, and they provide results in short duration.

The major drawback of one step lateral flow assays is their limited sensitivity. To obtain high assay sensitivity the assay should include several reaction steps including an enzymatic reaction step which amplifies the signal and preferably a washing step to reduce background and improve signal to noise ratio.

Performing multi-step assays in lateral flow devices may eliminate their major advantage which is short assay duration. Application and transport of several liquids serially through a typical capillary flow membrane substantially prolong the assay duration. The assay duration may be reduced by using high flow rate membranes, but such membranes have high pore size and relative low protein binding capacity, which results in low assay sensitivity. The efficiency of lateral flow based reactions is substantially affected by the receptor concentration immobilized in the capture zone.

From the above, it will be seen that it would be highly advantageous to have a lateral flow capillary device and method capable of performing rapid and simple reactions, particularly multi-step reactions, in the fields of biochemistry and medicine, particularly for research and diagnosis which avoid at least some of the above-discussed disadvantages of the prior art.

OBJECTS AND BRIEF SUMMARY OF THE PRESENT INVENTION

Objects of the present invention are to provide liquid-transfer devices particularly useful as capturing devices in methods for capturing a substance in a liquid, and particularly for use in biological assays, having advantages in one or more the above respects.

According to one aspect of the present invention, there is provided a liquid-transfer device, comprising: a lateral capillary flow matrix capable of producing a lateral capillary flow of the liquid via a capillary flow unipath from an upstream end to a downstream end of the capillary flow unipath; and at least one a liquid-transfer matrix having capillary passageways in fluid communication with the lateral capillary flow matrix such as to produce a lateral capillary flow through the capillary passageways in the liquid-transfer matrix having a lower lateral flow rate than that in the lateral capillary flow matrix, thereby producing, by the Bernoulli effect, a differential pressure with respect to the two lateral flows sufficient to impart transverse oscillation to the lateral flow in the capillary passageways of the liquid-transfer matrix, which oscillations drive the liquid into the interior of the liquid-transfer matrix, thereby exposing the interior of the liquid-transfer matrix, rather than merely a surface thereof, to the liquid.

According to another aspect of the present invention, there is provided a device for use in transferring a liquid including a first affinity molecule, comprising: a lateral capillary flow matrix capable of producing lateral capillary flow of the liquid via a capillary flow unipath from an upstream end to a downstream end of the capillary flow unipath; at least one inlet for loading the liquid onto the lateral capillary flow matrix at the upstream end; a liquid-transfer matrix carrying a second affinity molecule having an affinity to the first affinity molecule; the liquid-transfer matrix having capillary passageways in fluid communication with the lateral capillary flow matrix, such as to allow affinity interaction between the at least one first affinity molecule and the at least one second affinity molecule; the capillary passageways in the liquid-transfer matrix having a lower lateral flow rate than that in the lateral capillary flow matrix, thereby producing a differential pressure with respect to the two lateral flows sufficient to impart transverse oscillations to the lateral flow in the capillary passageways of the liquid-transfer matrix, which oscillations drive the liquid into the interior of the liquid-transfer matrix, thereby exposing the interior of the liquid-transfer matrix, rather than merely a surface thereof, to the liquid.

According to another aspect, the invention also provides a method of transferring a liquid using such a device.

As will be described more particularly below, the difference in the flow rates between the lateral capillary flow matrix and the liquid-transfer matrix controls the capture rate of the substance.

Many embodiments of the invention are described below for purposes of example. In all the described embodiments, the device further includes an absorbent body at the downstream end of the capillary flow unipath directing the lateral capillary flow through the capillary flow unipath at a higher flow rate than that produced in the liquid-transfer matrix thereby increasing, by the Bernoulli effect, the transverse oscillation flow into the capturing matrix In some described embodiments, the liquid transfer matrix is a capturing matrix wherein said device further comprises a capturing matrix in contact with a surface of said liquid-transfer matrix and having at least one capture zone capable of capturing a substance in the liquid from the oscillations in the flow through said liquid-transfer matrix.

In other described embodiments, the device further comprises wherein said liquid-transfer matrix is a capturing matrix defining at least one capture zone capable capturing a substance in the liquid from the oscillations in the flow through said capturing matrix.

Such devices and methods are particularly useful in biological assays, wherein the substance in the liquid to be captured is a biological substance. In some embodiments, such substances are captured for detection, examination, analysis purposes or other processing purposes, and in other embodiments, they are captured for producing a solid state reaction with an immobile reactant previously applied to the capture zone to produce a solid state reaction therein.

The substance in the liquid may be captured in the capturing matrix by the affinity of the capture zone with respect to the substance in the liquid, or by the size of the substance in the liquid. The capturing matrix may include a single capture zone, or a plurality of such zones sequentially spaced along the capillary flow unipath. The liquid to be examined may be introduced into the lateral capillary flow matrix by dipping; alternatively, the device may include an inlet defining a well serving as a reservoir for introducing the liquid. In addition, there may be a single inlet at the upstream end of the capillary flow unipath, or a plurality of inlets sequentially arrayed toward the downstream end for introducing a plurality of liquids sequentially or simultaneously.

As will be described more particularly below, such devices and methods enable the performance of rapid and simple reactions, both single-step and multi-step reactions, particularly, but not exclusively, in the fields of biochemistry and medicine, for research, diagnosis and/or testing purposes.

Thus, the device of the present invention may find use in assay methods for the determination of an analyte in a sample suspected of containing the analyte. The liquid reagent may be a single solution containing a second binding pair conjugated to a signal; such signal may be a colored particle of gold or latex. One may use several liquid reagents, the first containing a second binding pair conjugated to an enzyme and a second liquid reagent containing colored substrate which in the presence of the enzyme in the capture zone produces color. Such heterogonous reactions which contain several reagent solutions may interact between them or between them and the sample. This may occur as a result of entrapping of substances, for example in the lateral flow membrane having small pore size. The use of several reservoirs, one for the sample and other for reagents, reduces the interactions between them at least at the application zone, and thus improves sensitivity and specificity of the assay.

One heterogeneous solid phase reaction that may be used in the present invention is based on specific binding assays. Such a use has great value in a variety of clinical and other applications as described in U.S. Pat. No. 4,861,711, incorporated herein by reference. Specific binding assays involve the detection, and preferably quantitative determination, of an analyte in a sample where the analyte is a member of a specific binding pair consisting of a ligand and a receptor. The ligand and the receptor constituting a specific binding pair are related in that the receptor and ligand specifically mutually bind. Specific binding assays include immunological assays involving reactions between antibodies and antigens, hybridization reactions of DNA and RNA, and other specific binding reactions such as those involving hormone and other biological receptors. Specific binding assays may be practiced according to a variety of methods known in the art. Such assays include competitive binding assays, including "direct" and "indirect" sandwich assays as described, for example, in U.S. Pat. Nos. 4,861,711; 5,120,643; 4,855,240 and EP 284,232.

As indicated earlier, a very important advantage of the present invention over prior techniques is the production of the lower pressure between the two lateral flows, by the Bernoulli effect, sufficient to impart the transverse oscillation to the lateral flow in the capturing matrix, thereby driving the liquid into the interior of the capturing matrix for exposing the interior, rather than merely a surface, of the capturing matrix to the liquid.

Further features and advantages of the invention will be apparent from the description below.

BRIEF DESCRIPTION OF THE DRAWINGS

The invention is herein described, by way of example only, with reference to the accompanying drawings, wherein:

FIGS. 5A and 5B are exploded and assembled views, respectively, illustrating a further capillary flow device constructed in accordance with the present invention;

FIGS. 6A and 6B are exploded and assembled views, respectively, illustrating a still further capillary flow device constructed in accordance with the present invention.

FIG. 8B is a diagram illustrating the operation of the flow device of FIG. 8a;

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

THE PRIOR ART DEVICE OF FIG. 1

Figure 1:
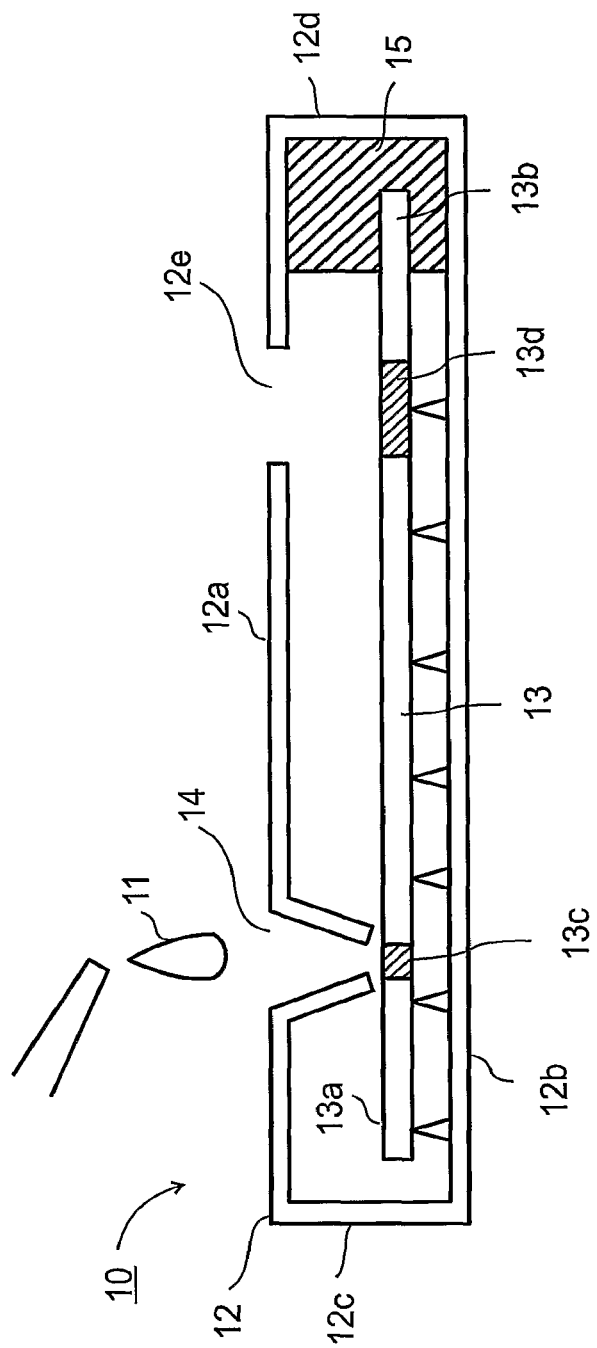
FIG. 1 is a side view diagrammatically illustrating one form of laterally flow capillary device as known in the prior art.

FIG. 1 illustrates a lateral flow capillary device, therein generally designated 10, well known in the prior art described in a companion application PCT WO2006/080021 assigned to the same assignee as the present application, the contents of which are incorporated herein by reference. Such a device is used particularly in the fields of biomarker detection by a quick and simple implementation of a specific binding assay of an analyte in a liquid sample 11. The lateral flow capillary device 10 includes a housing 12 formed with a top wall 12a, a bottom wall 12b, ends walls 12c, 12d, and side walls (not known). Disposed within housing 12 is a bibulous capillary flow matrix 13 defining a capillary flow unipath having an upstream end 13a adjacent to side wall 12c, and a downstream end 13b adjacent to side wall 12d. The upstream end 13a of capillary flow unipath 13 includes a receiving zone 13c underlying an inlet 14 in the top wall 12a of the housing for receiving the liquid sample 11, which forms a reservoir at inlet 14.

An absorbent body 15 is provided at the downstream end 13b of the capillary flow matrix 13 and serves to enhance the capillary flow of the liquid sample by capillary action along a unidirectional flow path towards the downstream end 13b of the matrix 13.

The downstream end of matrix 13 includes a capture zone 13d which is observable through an observation window 12e in the housing top wall 12a. Capture zone 13d includes an anti-analyte that together with the analyte in the liquid sample 11, constitutes a specific binding pair. Thus, the analyte in sample 11 forms a complex with the anti-analyte in capture zone 13d to produce a solid state reaction observable via window 12e. The so-produced reaction is related to the amount of analyte in the sample.

As indicated earlier, such a one-step lateral flow capillary device as illustrated in FIG. 1 is useful in one step lateral flow assays. However, to perform a multi-step binding assay using such a device liquid samples and liquid reagents are added serially to the inlet 14. For example, a liquid sample 11, which may contain an analyte of interest, is applied via inlet 14, passes into the capillary flow matrix 13 via the liquid receiving zone 13c, and then passes by lateral capillary action though capture zone 13d. If the sample includes the analyte present of interest, it forms a complex with the anti-analyte located in the capture zone 13d observable via window 12e. After the sample 11 has been completely drained from the capillary flow matrix 13, a first liquid reagent, containing a labeled reagent capable of binding to the analyte, is added through inlet 14 and is transported by capillary flow to the capture zone 13d. The labeled reagent in that liquid binds to the analyte (or analytes) previously captured at the capture zone 13d to produce a solid state reaction observable via window 12e.

For example, when the reagent in the latter liquid includes an enzyme, another liquid containing an enzyme substrate would be added via inlet 11 and passes through capture zone 13d, wherein the enzyme substrate therein reacts with the enzyme label, producing a signal via observable window 12e. The intensity of the observable signal is related to the amount of analyte in the sample.

As indicated earlier, the use of the prior art capillary flow device illustrated in FIG. 1, particularly when used for multi-step assay processes, is both labor and time consuming.

DESCRIPTION OF PREFERRED EMBODIMENTS

Features Common to All the Described Embodiments

The embodiments of the invention illustrated in the drawings are designed for performing accelerated heterogeneous solid phase reactions in a simple and rapid procedure, and are therefore particularly useful for both single-step and multi-step chemical processes involving biomolecule manipulations. Such manipulations may include modification, isolation, extraction, fractionation, identification, diagnosis, etc.

For example, the diagnostic process may be conducted in respect of an analyte in the form of an antigen, antibody or nucleic acid within a body fluid, such as blood or urine, of which a sample is made available. The analyte may first be specifically bound with the capturing molecule, such as an antibody immobilized at the capture zone, then labeled by a first reagent, and finally subjected to a label detection by a second reagent, to make a calorimetric or other output available. Such an analytical procedure is appropriate for a wide range of analytes of diagnostic interest, and so represents a practical basis for exemplifying the invention in the embodiments of the invention described herein.

It will be appreciated, however, that the specific embodiments described herein, are set forth merely for purposes of example, and that the invention can be implemented in many other embodiments and applications.

In all the described embodiments, there is provided a liquid-transfer device particularly useful as a capturing device for use in capturing a substance in a liquid. The liquid-transfer device comprises:

(a) a lateral capillary flow matrix capable of producing a lateral capillary flow of the liquid containing the substance via a capillary flow unipath from an upstream end to a downstream end of the capillary flow unipath; and (b) a liquid-transfer matrix having capillary passageways in fluid communication with the lateral capillary flow matrix to produce a lateral capillary flow in the liquid-transfer matrix having a lower flow rate than that in the lateral capillary flow matrix. Generally, there should be a full planar contact between the two matrices, either directly or indirectly. The two matrices have different lateral flow rate properties, The higher flow rate in the lateral capillary flow matrix produces, by the Bernoulli effect, a lower pressure between the two lateral flows sufficient to impart a transverse oscillation to the lateral flow in the liquid-transfer matrix, which oscillations drive the liquid into the interior of the liquid-transfer matrix, thereby exposing the interior of the capturing matrix, rather than merely a surface thereof, to the liquid.

Preferably, each of the matrices is formed with small capillary flow passageways defined by the interstices between small-diameter filaments of the respective matrix. It will be appreciated, however, that in some applications of the invention, one or both of the matrices may include capillary passageways in the form of interconnecting pores, ribs defining small guiding channels, or roughened or etched surfaces defining the capillary passages.

In embodiments of the present invention the lateral capillary flow matrix may be composed of materials enabling lateral capillary liquid flow, such materials may be porous or bibulous material such as glass fiber, plastic polymers, such as polyethylene, Cellulose, Nitrocellulose, and the like. The lateral flow rate of such materials depends mainly on the void volume and porosity of the matrix. Such matrices can be of fibrous nature, such as glass or cellulose microfiber structures having a wicking rate of 20-200 s/4 cm, preferably 20-70 s/4 cm (raise time of water inside the membrane). In case of material having pores, the pore size is preferably in the range of 1-15 μm.

In embodiments of the present invention the liquid-transfer matrix (e.g., capture matrix) may be composed of materials with relatively low lateral capillary flow properties, nylon, Polyvinylidene fluoride (PVDF) Nitrocellulose and Niotrocellulose mixed Esters. These materials have low pore sizes typically in the range of 0.1 μm-5 μm but preferably in the range of 0.1 μm-0.45 μm.

According to one embodiment, the lateral capillary flow rate of the lateral capillary flow matrix is at least twice, preferably at least live times, more preferably at least 10 times faster then that of the liquid-transfer matrix.

In other described embodiments of the present invention, the capturing matrix may be a separate layer applied over the liquid-transfer matrix and composed of a non-porous, non-water permeable materials, such as glass, plastic, ceramics silicon or metal and the like. The surface of such capturing matrices may be smoothed, but are preferably roughened and comprise grooves which are perpendicular to the surface. Such grooves and textured surface increase the capability to transfer liquid by capillarity.

It will be appreciated that the capturing matrix may be able to capture a substance by virtue of an intrinsic property (e.g. pore size, charge, etc.), or may comprise a capturing molecule which is able to capture (e.g. bind to) a second molecule.

The capturing matrix has at least one capture zone capable of capturing (e.g. localizing or immobilizing) the substance from the oscillating flow therethrough. The mechanism of action involved in such a construction will be more particularly described with respect to FIGS. 3 and 8b.

The capture zone of the capturing matrix may have several types distinct sites, usually in the shape of spaced lines. When the capturing matrix comprises more than one capture zone, each capture zone may comprise an identical or a non-identical capturing molecule.

Preferably, the device further includes an absorbent body at the downstream end of the lateral capillary flow unipath for absorbing the liquids, directing the flow in the unipath and enable continues downstream lateral flow. It will be appreciated that the absorbent body may be an integral part of the lateral capillary flow matrix (e.g. an extension of the lateral capillary flow matrix), or a separate body (e.g. Cellulose pad). According to one embodiment, the absorbent layer is comprised of the identical material used in the lateral capillary flow matrix, but is thicker in width. Whatever the material used for the absorbent body, typically the absorbent body has high liquid retention properties and high void volume and high wicking rate equal or higher than the lateral capillary flow matrix.

It will be further appreciated that other means can be used for maintaining the higher lateral capillary flow rate, for example, by subjecting the downstream end of the lateral capillary flow matrix to a vacuum.

Selection of the material used to fabricate the capturing matrix is typically dependent on the particular substance (e.g. biological substance) that one desires to capture. Selection of the material used to fabricate the lateral capillary flow matrix is typically dependent on the material used to fabricate the capturing matrix, the efficiency of the absorbent (if present) and is restricted to a material that in combination with the capturing matrix (and optional absorbent) produces a Bernoulli effect. Typical parameters that must be taken into account when deciding whether a combination of two particular materials are capable of producing the Bernoulli effect include, but are not limited to, the permeability/porosity and wicking rate of the materials.

As indicated earlier, such a substance may be captured for detection, examination and/or analysis purposes, or for use in producing a solid phase reaction with another substance in another liquid introduced into the device captured in the capture zone of the capturing matrix.

As further indicated above, such a capillary flow device is particularly useful in biological assay procedures, and is therefore described below with respect to such a procedure.

Figure 2:
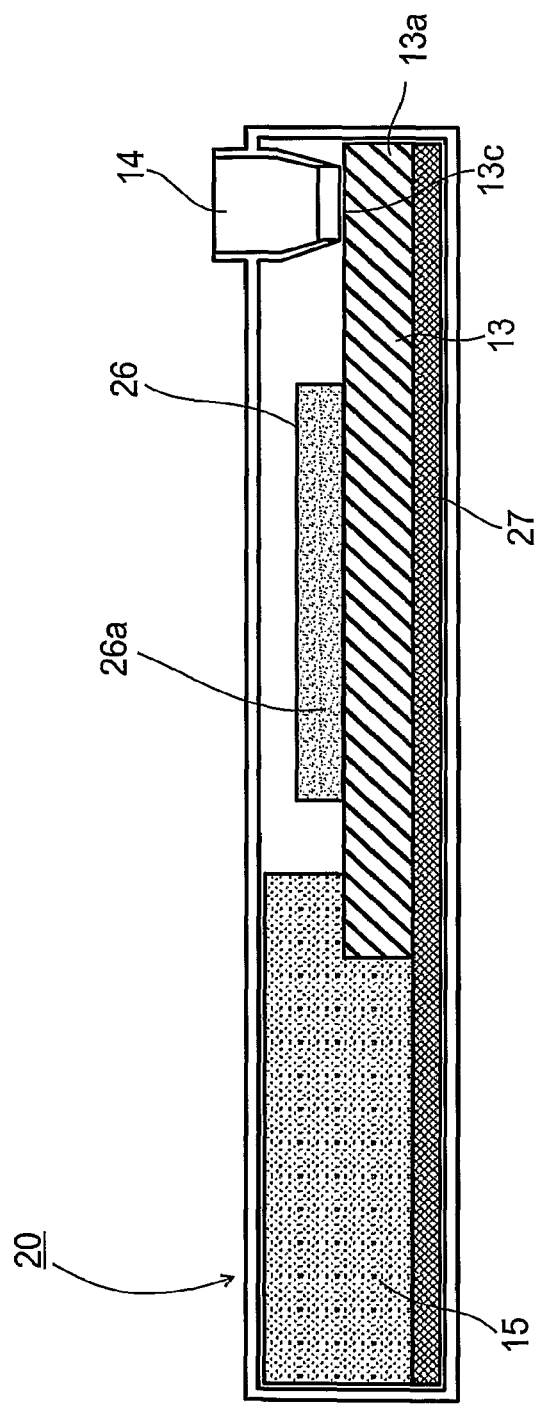
FIG. 2 diagrammatically illustrates a capillary flow device constructed in accordance with the present invention.
Figure 3:
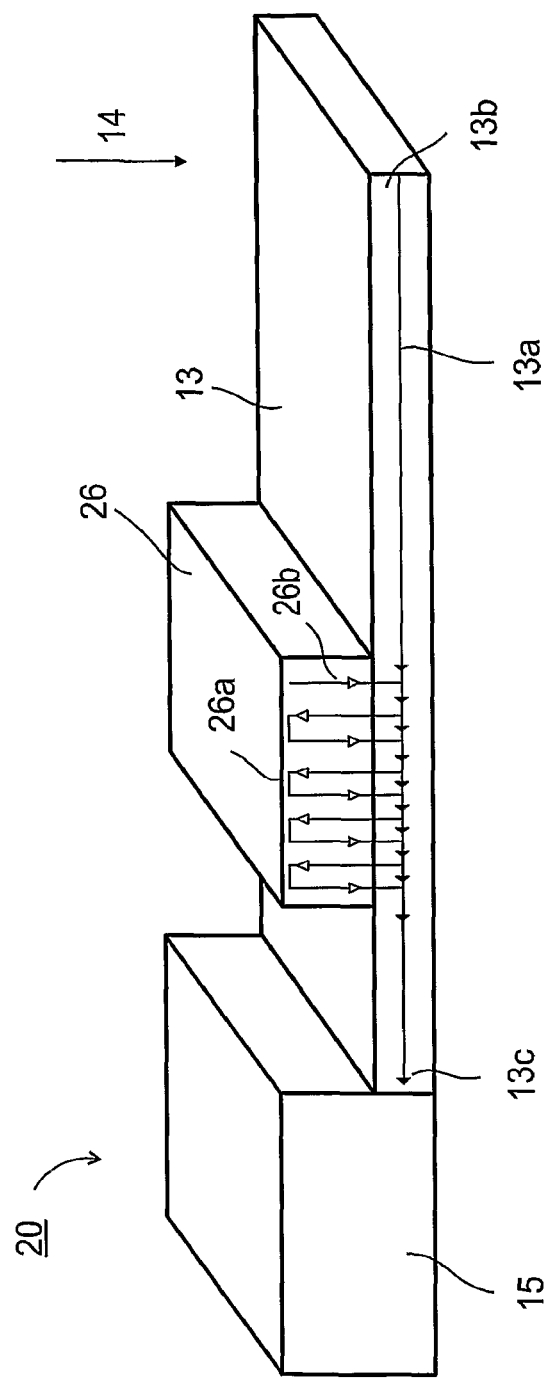
FIG. 3 is a diagram helping to explain how the transverse oscillations are imparted to the lateral capillary flow to drive the liquid into the interior of the capturing matrix, to thereby expose the interior of the capturing matrix, rather than merely a surface thereof, to the liquid being examined.

The FIGS. 2 and 3 Embodiments

FIG. 2 illustrates an embodiment of a capillary flow device constructed in accordance with the present invention; and FIG. 3 is a diagram explaining the mechanism of action in the FIG. 2 embodiment.

The capillary flow device illustrated in FIG. 2, generally designated 20, includes the same elements as described above with respect to the prior art device 10 of FIG. 1, i.e. the lateral capillary flow matrix 13, the inlet thereto 14, and the absorbent body 15, and therefore, for purposes of convenience, these parts are identified by the same reference numerals. The main difference in the novel device 20 of FIG. 2, as compared to the prior art device 10 of FIG. 1, is that the FIG. 2 device includes a capturing matrix 26 having at least one capture zone 26a in fluid communication with the lateral capillary flow matrix 13 (i.e. between the upstream and downstream ends of lateral capillary flow matrix 13), which overlies a plastic layer 27.

The capturing matrix comprises the capture zone and may have several types of distinct sites, usually in a shape of lines.

It is to be particularly noted that the Bernoulli effect is generated because of the difference in the matrix lateral flow rate properties and not because of absorbent lateral flow properties. The absorbent enables to maintain the flow along the assay period.

The lateral capillary flow matrix 13 has a higher lateral flow rate than the capturing matrix 26; that is, the flow velocity through the capturing matrix is lower than that through the lateral capillary flow matrix. Such difference in flow rates produces, by the Bernoulli effect, a differential pressure with respect to the two lateral flows, sufficient to impart a transverse oscillation to the lateral flow in the capturing matrix 26. Such an oscillation draws the liquid into the interior of the capturing matrix 26, thereby exposing the interior of that matrix, rather than merely a surface thereof, to the liquid. Thus, each of the capture zones, e.g. capture zone 26a, of the capturing matrix 26 is more effectively capable of capturing the substance in the liquid by binding molecules thereto.

For operating the device, the liquid sample is applied to the reservoir, the liquid drains into the lateral capillary flow unipath 13a through the receiving zones 13c and flow through the two matrixes towards the absorbent, resulting in a binding reaction between the analyte, if present in the sample, and the capturing molecule immobilized on the capturing zone. When the entire sample is drained from the reservoir into capillary flow unipath, the next liquid participating in the reaction (LPIR) is applied into the reservoir which migrates through the capillary flow unipath performing a second reaction on the capturing zone. The process is repeated until the last LPIR drains from the reservoir. In a sandwich type immunoassay, in the first step sample fluid may be applied to the reservoir; in the second step a solution containing an enzyme labeled reagent having affinity toward the analyte is applied into the reservoir and in the third step liquid containing signal producing component such as enzyme substrate is applied. The flow takes place in the capillary flow unipath whilst the reaction takes place on the capturing zone of the capturing matrix.

The mechanism of the foregoing action is more particularly illustrated in the diagram of FIG. 3, showing the capillary flow unipath 13a of the lateral capillary flow matrix 13, and the capillary interior flow path 26b of the capturing matrix 26 having at least one capture zone 26a. The capillary interior flow path 26b is generated by the low pressure produced by the Bernoulli effect in the capillary flow unipath 13a of the lateral capillary flow matrix 13. The capillary interior flow path 26b is of a transverse oscillation type, as shown at 26b.

In operating of the illustrated device, wherein two matrices are provided, one (13) of a high flow rate and a second matrix 26 of a lower flow rate but of a higher capacity to bind biomolecules, two phenomena were unexpectedly observed: (a) the capturing matrix 26 exhibited no substantial effect on the total lateral flow rate or duration of the test, and (b) the signal intensity generated on the surface of the capturing zone was not substantially affected by the direction in which the capturing matrix was placed on the lateral capillary flow matrix, that is, whether the capture zone (26a) at which the substance was captured was on the same side of the capturing matrix 26 in contact with the lateral capillary flow matrix 13, or on the opposite side.

These two observations indicate that in parallel to the lateral flow taking place in the lateral capillary flow matrix 13, there is an oscillatory transverse flow between the two matrices. These observations also indicate that the lateral flow depends on the flow rate through the lateral capillary flow matrix 13, and that the transverse flow is mainly influenced by the slower lateral capillary flow through the capturing matrix 26. The driving force for the lateral flow through matrix 13 is the water potential differences generated by the dry nature of the downstream zone 13c mainly caused by the absorbent 15; whereas the driving force for the transverse oscillations of the capillary flow in the capturing matrix 26 is also the lateral flow in the lateral capillary flow matrix 13, which is faster than the lateral flow in the capturing matrix 26. According to the Bernoulli principle, the pressure is lower in the faster flow taking place at the lateral capillary flow matrix. As a result, a downward flow from the capturing matrix 26 into the lateral capillary flow matrix 13 takes place, and as a result of the downward flow, liquid is evacuated from the capturing matrix causing an opposite force leading to an upward flow in the capturing matrix. This phenomenon repeats itself, thus generating the transverse oscillation in the capturing matrix 26, as shown by the flow path 26b through that matrix. The effect was found to be more profound as the flow rate ratio between the two matrices was increased.

In the embodiment of the present invention illustrated in FIGS. 2 and 3, the capture matrix 26 is positioned beneath inlet 14 on top of lateral capillary flow matrix 13. Also, the capture matrix 26 is in direct contact with the lateral capillary flow matrix 13, and matrix 13 is in direct contact with the absorbent pad 15.

Figure 4A:
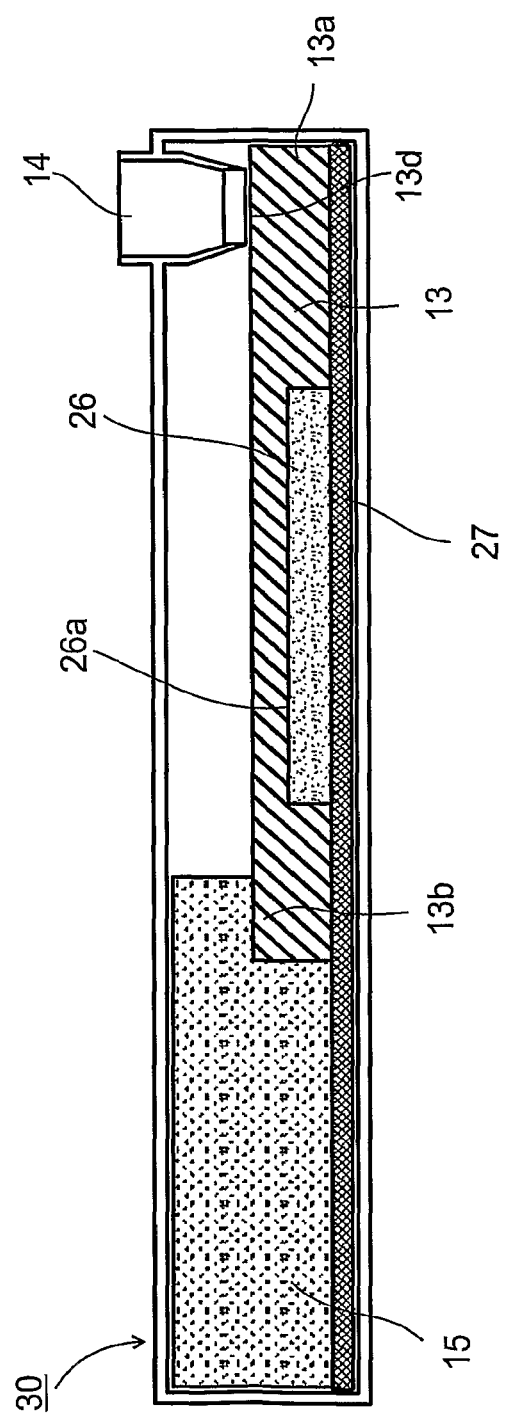
FIGS. 4A and 4B illustrate two variations of the capillary flow device of FIG. 2.
Figure 4B:
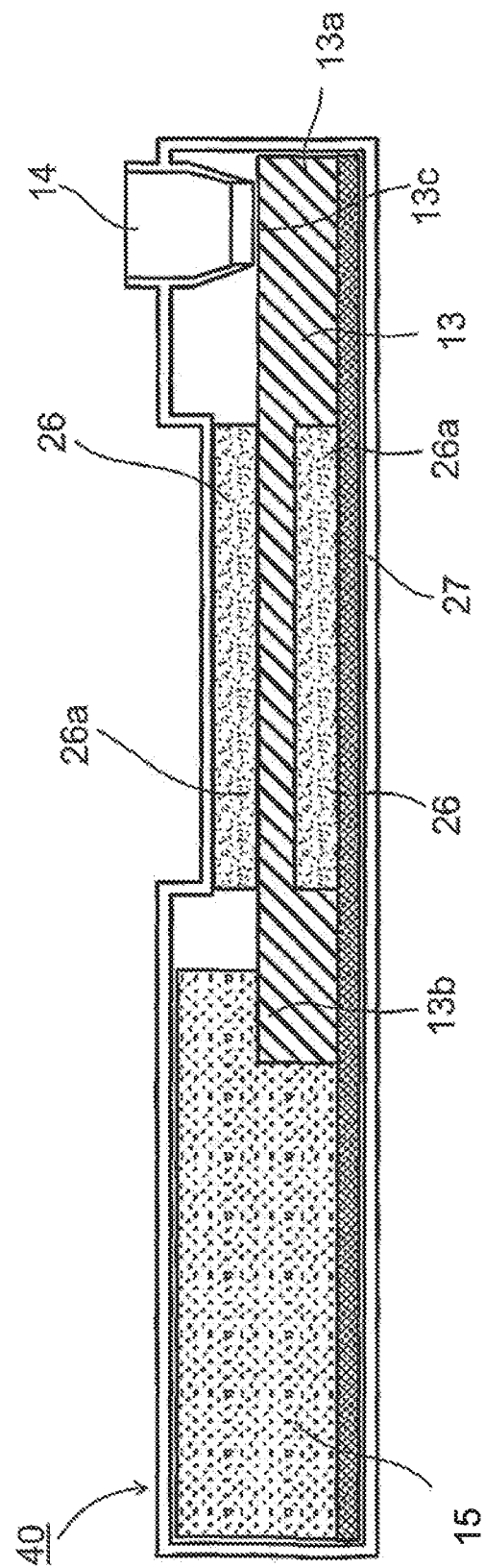

The FIGS. 4a and 4b Embodiments

FIGS. 4a and 4b illustrate two variations in the capillary flow device of FIGS. 2 and 3. Whereas in FIGS. 2 and 3, the capturing matrix 26 is applied over the upper face of the lateral capillary flow matrix 13, in the device of FIG. 4a, generally designated 30, the capturing matrix 26 is interposed between the lower face of the lateral capillary flow matrix 13 and the underlying plastic layer 27; and in FIG. 4a, a capturing matrix 26 is applied to each of the two opposed faces of the lateral capillary flow matrix 13. Otherwise, the constructions and operations are substantially the same.

When the devices depicted in FIGS. 2-4b are used for immunoassays, the lateral capillary flow matrix and the capturing matrix are of a strip shape. Capturing molecules such as anti-analyte antibodies are immobilized to the capturing zone. A liquid sample is applied to the inlet and flows downstream through the lateral capillary flow matrix, penetrating into the capturing matrix, and continuing to flow toward the absorbent. During the flow, the analyte (if present in the sample) is captured by the molecules immobilized on the capturing zone of the capturing matrix.

As the sample drains out from the reservoir, the second liquid is applied. Such a liquid may be a conjugate solution composed of enzyme conjugated to anti-analyte antibody. The conjugate solution then flows through the lateral capillary flow matrix penetrating into the capturing matrix thus enabling the capture of the conjugate to the anti analyte—analyte complex attached on the capturing zone. As the second liquid drains out from the reservoir, a third liquid containing an enzyme substrate is applied. The liquid flows through the lateral capillary flow matrix and into the capturing matrix so that a signal is produced on the capturing zone. In the present invention one matrix, the lateral capillary flow matrix, is serving as a liquid reagent-transport matrix and the other matrix, the capturing matrix, serves as a platform for the reactions. The reactions which are solid phase type reactions take place on the matrix which is not driving the liquid flow. This unusual method has the advantage of selecting the preferred membrane for each function. High protein (and other capture molecules) binding membrane usually of low pore size and low capillarity is used to fabricate the capturing matrix and an effective transport membrane usually of high pore size is used to fabricate the lateral capillary flow matrix.

In FIG. 4b, the device illustrated therein, generally designated 40, includes two capturing matrices 26, one in contact with the upper face of the lateral capillary flow matrix 13, and the other in contact with the under face of the lateral capillary flow matrix 13, between it and the underlying plastic layer 27. The capture substances or molecules captured in the two capturing matrices 26 may be the same, or different. The device illustrated in FIG. 4b is otherwise constructed and operates in substantially the same manner as described above with respect to FIGS. 2 and 3.

The FIGS. 5a-6b Embodiments

FIGS. 5a and 5b are exploded and assembled views, respectively, of a further capillary flow device, generally designated 50, constructed in accordance with the present invention. The device therein illustrated includes a two-part housing, in which one part includes the top wall 52a, the two end walls 52c and 52d, and the side walls (not shown), whereas the bottom part includes the bottom wall 52d detachable from the top part including the top wall 52a. Such a two-part construction permits convenient access to the various elements within the housing.

Thus, disposed within the housing is a lateral capillary flow matrix 53 having a plastic under layer 57, and defining a capillary flow unipath having an upstream end 53a adjacent to side wall 52c, and a downstream end 53b. The upstream end 53a of the lateral capillary flow matrix unipath includes a receiving zone 54 underlying an inlet 55 in the top wall 52a of the housing for receiving the liquid sample 51, which forms a well or reservoir in inlet 55.

In this case, the absorbent body is constituted of a plurality of sections, 55a-55c, one section 55a overlying the upper surface of the downstream end of the lateral capillary flow matrix 53, and the other two sections 55b, 55c, underlying the upstream end 53b of matrix 53. The inner surface of the top wall section 52a of the housing is formed with inwardly-extending ribs 52f overlying the absorbent body sections 55a-55c so as to be engageable with the upper section 55a, when the housing is assembled as shown in FIG. 5b, to firmly press the absorbent body sections toward each other, and thereby to firmly sandwich the downstream end 53b of the lateral capillary flow matrix 53 between them. In addition, the bottom housing wall 52b is formed with an inwardly-extending step 52g to firmly clamp the upstream end of the lateral capillary flow matrix 53 between it and the inner rim of the inlet 55.

Device 50 illustrated in FIGS. 5a and 5b further includes a capturing matrix 56 overlying the lateral capillary flow matrix 53 and having a capture zone 56a in fluid communication with the lateral capillary flow matrix. As in the previously described embodiment, the capture zone 56a is capable of receiving, by transverse capillary flow, a part of the liquid from the lateral capillary flow through matrix 53, and is designed so as to be capable of capturing the substance in the part of the liquid 51 received from the lateral capillary flow matrix 53.

In all other respects, the device illustrated in FIGS. 5a and 5b is constructed and operates in substantially the same manner as described above with respect to the embodiments of FIGS. 2-4.

An exemplary material envisaged for the housing of the devices of the present invention is. Typically, the housing is comprised of a water resistant material and one which can be molded into a particular shape.

FIGS. 6a and 6b are views, corresponding to those of FIGS. 5a and 5b, illustrating a further embodiment of the invention, which is very similar to that of FIGS. 5a and 5b. Accordingly, for the sake of convenience, those parts in FIGS. 6a and 6b which generally correspond to the parts in FIGS. 5a and 5b are identified by the same reference numerals.

The main difference in the device 60 illustrated in FIGS. 6a and 6b, over that of FIGS. 5a and 5b, is that whereas the lateral capillary flow matrix 53 in FIGS. 5a and 5b underlies the capturing matrix 56, in the device 60 of FIGS. 6a and 6b, the lateral capillary flow matrix 63 overlies the capturing matrix 56, the latter being interposed between the underside of matrix 63 and the plastic under layer 67 for the lateral capillary flow matrix 63. In substantially all other respects, device 60 illustrated in FIGS. 6a and 6b is constructed and operates in substantially the same manner as described above with respect to FIGS. 5a and 5b.

The devices depicted in FIGS. 5a-b and 6a-b may be useful for lateral flow based immuno-development of Western blot membranes. Dimensions of the immuno-blot development device may be selected such that they are useful for standard Western blot membrane dimensions (mini gel or normal gel membrane) as well as for cases where the user is interested in development of only part of the membrane blot. The operation of the device involves cutting the blotted membrane into strips. Operation of the device for development of blotting membrane or strips includes assembly of the device depicted in FIGS. 5a-5b and 6a-6b and using the blotted membrane as the capturing membrane. To operate the device, the LPIRs are applied into the reservoir according to the development protocol. Each solution is allowed to drain completely before the next solution is applied. Upon assay completion, the plastic housing is opened and the developed membrane is visualized.

In embodiments of the present invention the method and the devices depicted in FIGS. 5a-6b and 6a-6b may be used for Southern blot membrane development.

It will be appreciated that the above described devices may be in the shape of a dip stick comprised of lateral capillary flow matrix, capturing matrix and optionally an absorbent. The capturing matrix may be between the lateral capillary matrix and the plastic backing support it may also be above the lateral capillary flow matrix. Operation of such a device involves application of LPIR into a reservoir and dipping the upstream end of the dip stick into the solution.

In embodiments of the present invention the above described device configurations may comprise at least two reservoirs each in fluid communication with the capillary flow unipath enabling a sequential synchronized LPIR flow as described in patent application PCT/IL 2006/000121, the contents of which are hereby incorporated by reference.

The Embodiments of FIGS. 7-12

Figure 7:
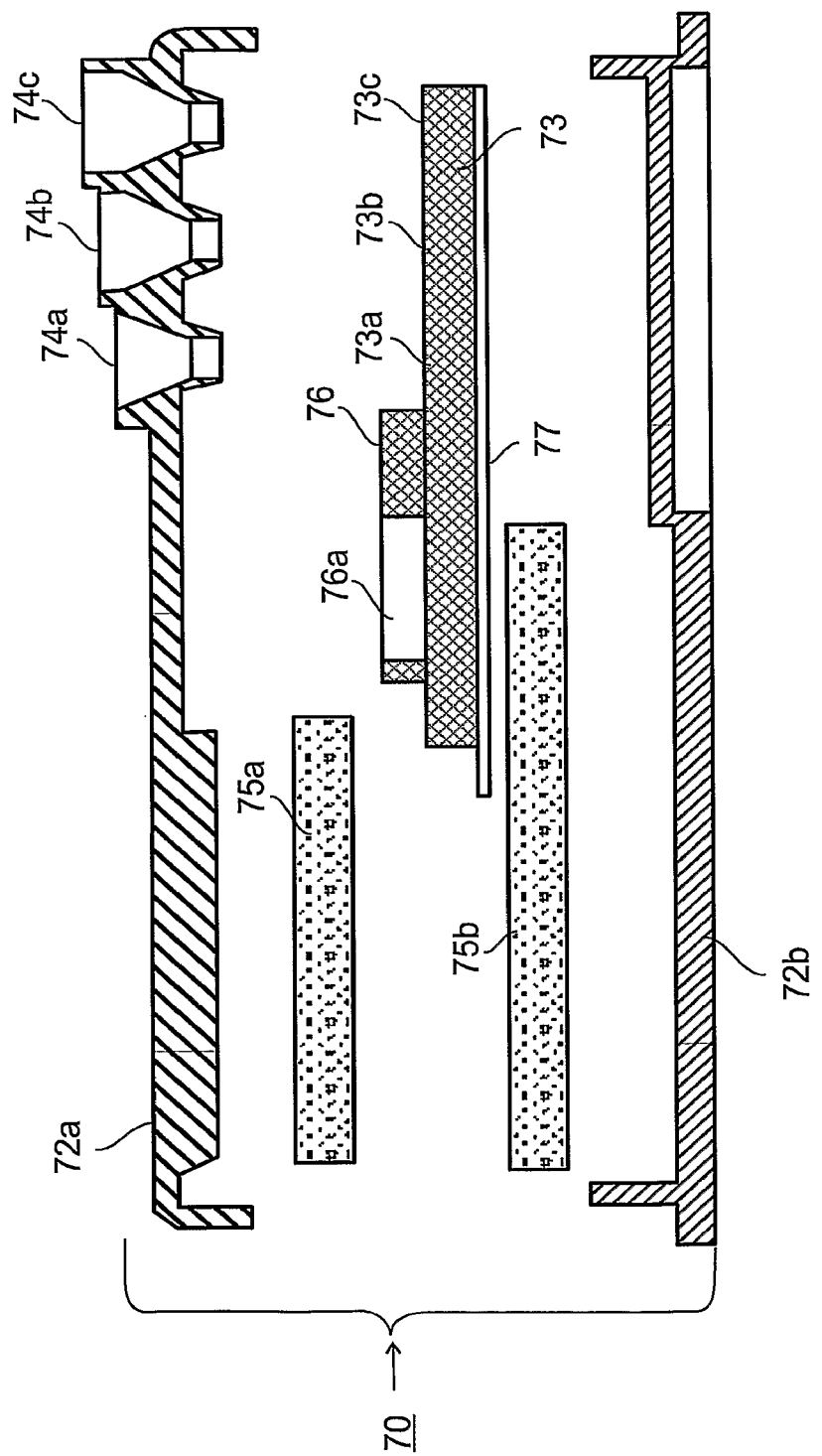
FIG. 7 is an exploded view illustrating another capillary flow device constructed in accordance with the present invention.

FIG. 7 is an exploded view of a capturing device, generally designated 70, similar to that of device 60 in FIGS. 6a and 6b. Thus, the device illustrated in FIG. 7 also includes a two-part housing 72a, 72b for a lateral capillary flow matrix 73 having its downstream end sandwiched between a plurality of absorbent bodies, 75a, 75b to direct the lateral flow of liquid therethrough. In this case, the capturing matrix 76 overlies the lateral capillary flow matrix 73 having a plastic under layer 77, with the capturing reagent 76a of the capturing matrix downstream of the lateral capillary flow matrix 73.

Also in this case, the top housing section 72a is formed with a plurality of inlets 74a, 74b, 74c, spaced from each other with respect to the lateral flow through the lateral capillary flow matrix 73, and define three liquid receiving zones 73a, 73b and 73c, respectively. As shown in FIG. 7, the first inlet 74a is closest to the downstream end of the lateral capillary flow matrix 73, whereas inlet 74c is closest to the upstream end of the lateral capillary flow matrix.

The operation of device 70 illustrated in FIG. 7 is similar to those described above, except that, in this case, three liquids are introduced simultaneously or almost simultaneously into the three inlets 74a, 75b and 74c respectively. The liquids introduced via inlets 74a, 74b, 74c, are received by the lateral capillary flow matrix 73 in the liquid receiving sections 73a, 73b and 73c, respectively and flow through the capture matrix 76 in a sequential manner. For example, in an assay for detecting an antigen in the sample, the capture reagent may be an antibody having affinity toward the antigen in the sample. The first liquid may be introduced via inlet 74*a* and may contain the antigen in the sample to be captured in capture region 76*a* of the capturing matrix 76; the second liquid may be introduced via inlet 74*b* and may contain a conjugate of the second antibody having an affinity toward the antigen conjugated to an enzyme; and the third liquid introduced via inlet 74*c* may include a third liquid reagent containing a colored substrate which in the presence of the enzyme in the capturing zone 76*a* produces color.

Figure 8A:
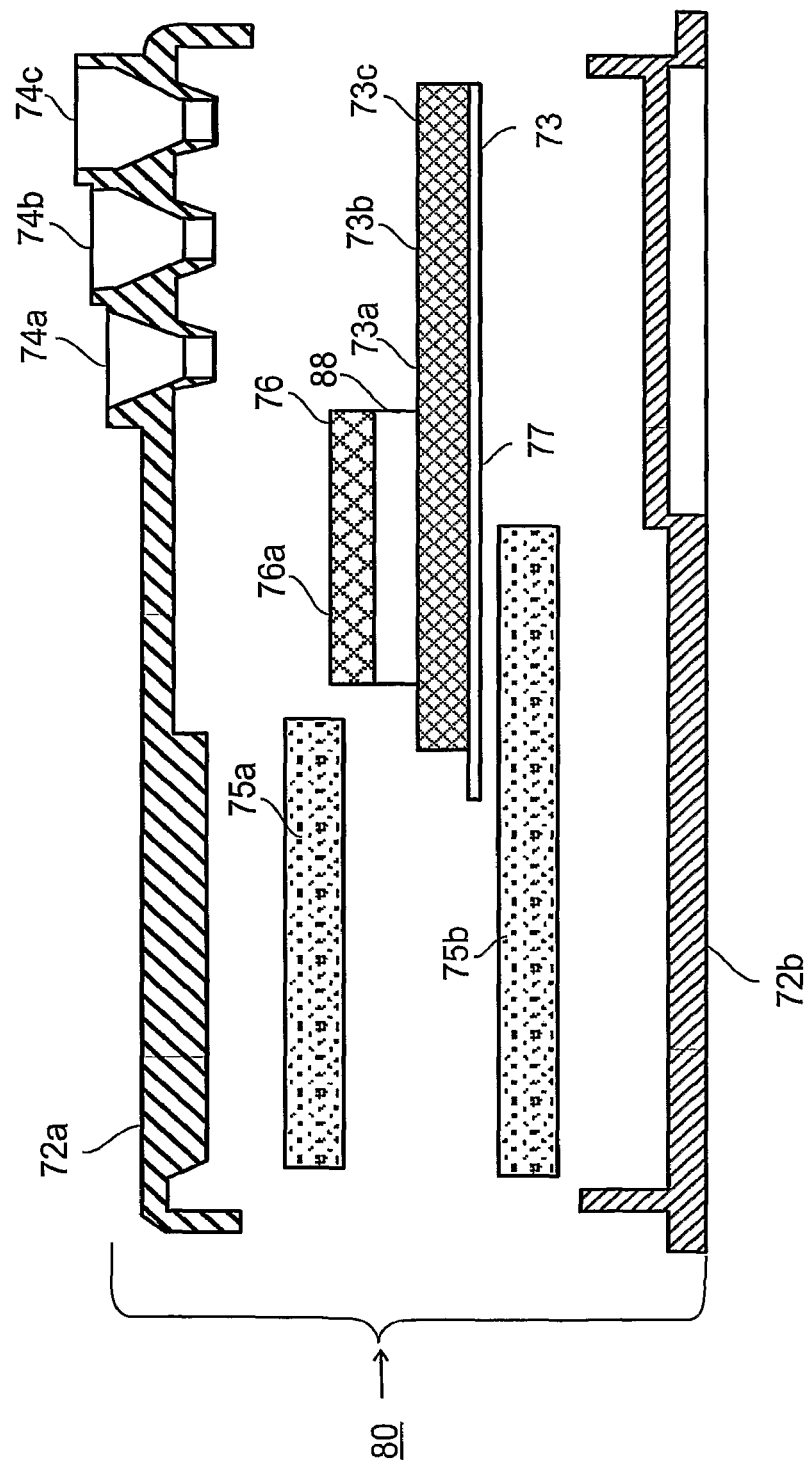
FIG. 8A is an exploded view illustrating a still further capillary flow device constructed in accordance with the present invention.

FIG. 8*a* is an exploded view of a still further capturing device constructed in accordance with the invention, which is generally similar to that of FIG. 7, and therefore for convenience, the elements in FIG. 8*a* corresponding to those of FIG. 7 are identified by the same reference numerals.

The main difference between the two constructions is that, whereas in FIG. 7, the capture zone 76*a* of the capturing matrix 76 communicates with the lateral capillary flow matrix 73 by direct contact between the two matrices, in FIG. 8*a*, the capturing zone 76*a* of the capturing matrix 76 is in communication with the lateral capillary flow matrix 73 via an intermediate liquid-transfer matrix 88 capable of producing a transverse oscillating flow therethrough from the lateral capillary flow matrix 73 to the capture zone 76*a* of the capturing matrix 76. The intermediate member 88 is in full contact with the capillary flow unipath of the lateral capillary flow matrix 73 downstream from each of the liquid receiving zones 73*a*, 73*b*, 73*c* of matrix 73.

Another embodiment of the invention would include a second capture matrix having a capture zone positioned in full contact on top of the first capture matrix, that is, in full communication with the lateral capillary flow matrix, for performing a simultaneously second capture reaction of same type or of different type. A still further embodiment would include a second intermediate matrix positioned in full contact on top of the first capture matrix, that is, in communication with the lateral capillary flow matrix via a first intermediate member and a second capture matrix having capture zone would be positioned in full contact with the second intermediate matrix, for performing a simultaneously second capture reaction of same type or of different type.

Figure 8B:
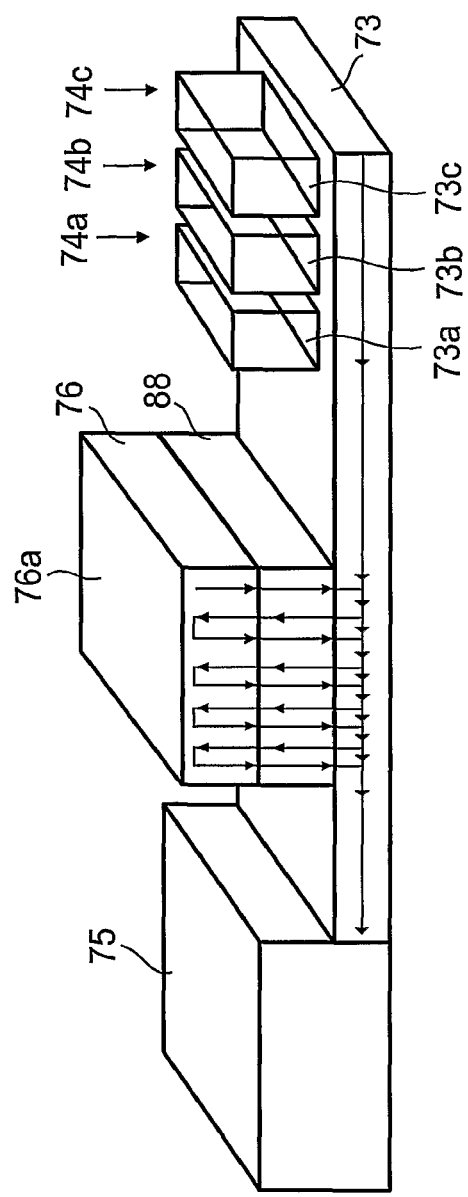

FIG. 8*b* is a diagram, similar to that of FIG. 3, explains the mechanism of action involved in the device of FIG. 8*a*. Thus, FIG. 8*b* illustrates the intermediate member 88, between the capturing matrix 76 and the lateral capillary flow matrix 73, which is capable of producing the transverse oscillating flow from matrix 73 to the one or more capture zones 76*a* of the capturing matrix 76. As shown in FIG. 8*b*, the intermediate liquid-transfer matrix 88 is in full contact with the capillary flow unipath of the lateral capillary flow matrix downstream of the liquid receiving zones 73*a*, 73*b* and 73*c*, and conducts, by the transverse oscillations produced by the differential pressure between the flow of the two matrices as described above, the liquid to the one or more capture zones 76*a* of the capturing matrix 76.

During use of the illustrated device, the liquids are applied simultaneously or almost simultaneously to the device via the inlets 74*a*-74*c* contacting the lateral capillary flow matrix 73 at their respective liquid receiving zones 73*a*-73*c*. Static interfaces are formed between the first and second liquids in zones 73*a*, 73*b*, and between the second and third liquids in zones 73*b*, 73*c*. Such interfaces begin to move only subsequent to exhaustion of the liquid from the respective wells or reservoirs produced at their respective inlets 74*a*-74*c*.

Sequential flows then take place in the lateral capillary flow matrix 73 producing multi-step reactions in the capture zone 76*a* of the capturing matrix 76. First, liquid from inlet 74*a* drains through the liquid receiving zone 73*a* and flows downstream through the intermediate liquid-transfer matrix 88 and capturing matrix 76 to the capture zone 76*a*, where the analyte, or other substance to be captured, if present, is captured while the remaining liquid drains into the absorbent body 75. Then, the first liquid/second liquid interface begins to move downstream, and the second liquid from the middle inlet 74*b* flows via the intermediate liquid-transfer matrix 88 and the capturing matrix 76 to the capture zone 76*a*, while the remaining liquid drains into the absorbent body 75. When the second liquid has drained completely from inlet 74*b*, the second liquid/third liquid interface begins to move downstream as described above, to drain into the absorbent body 75 while the substance or molecule contained in the third liquid is fed, via the illustrated transverse oscillating flow, through the intermediate liquid-transfer matrix 88 to the capture zone 76*a* of the capturing matrix 76.

In order to follow the flow, three differently colored solutions were applied to the three inlets of the device. It was observed that the liquid/liquid interfaces move simultaneously along the lateral capillary flow matrix and in the liquid-transfer matrix.

Accordingly, multi-step reactions of different types may be performed on the configuration illustrated in FIGS. 8*a* and 8*b*, including diagnostic assays, Western and Southern blot development assays, biomolecule modification reactions, biomolecule purification, assays performed on microscope slides, and microarrays assays. It has been found that the provision of the intermediate liquid-transfer matrix 88 substantially improves two assay properties when compared to the devices not using such an intermediate matrix. First, the background signal is reduced; and secondly, the signal appearance has been improved.

The intermediate liquid-transfer matrix 88 preferably has lateral capillary flow properties higher than that of the capturing matrix 76, but lower than the lateral capillary flow matrix 73. Preferably, all three matrices are in the form of membranes in contact with each other and preferably the capture matrix is in full planar contact with the intermediate liquid-transfer matrix which is in full planar contact with the lateral capillary flow matrix.

A successful combination of matrices, for example, would be a capturing matrix 76 of nitrocellulose or Polyvinylidene fluoride PVDF with very small pore size of 0.2 microns and extremely low lateral flow rates; an intermediate membrane 88 of polyethylene (Porex) having a typical thickness 0.010 inches (0.0254 cm), of medium pore size of 8 microns and having a smooth surface; and a lateral capillary flow matrix 73, of glass fiber having fine porosity, fast flow rate, a typical thickness around 435 microns, a smooth surface made of borosilicate glass microfiber, and a high void volume, and a high liquid absorption.

In the described embodiment, the capturing matrix 76 is a microscope slide. The device and method are useful for microscopic slide manipulation, including cytological and histological treatments, which treatments may be cells and tissue staining; immunoassays performed on slides, in-situ hybridization, DNA and RNA hybridization assays performed on slides. The slides may be fabricated from glass or plastic, or may be covered by porous material such as nitrocellulose.

The devices illustrated in FIGS. 8 and 8*a* are useful for nucleic acid (N.A.) extraction. The capturing matrix 76 may be a silica activated membrane (e.g. Sigma Aldrich, USA), which enables different DNA and RNA binding properties. For example, DNA may be extracted from the biological samples, such as blood, urine and different types of tissues.

Such DNA extractions would typically involve three types of reactions: DNA release, binding of the release DNA to a solid phase, and release of the DNA from the solid phase.

The main function of the first liquid applied to reservoir 74a is to delay the flow of the liquid applied to reservoir 74b, and thus enables the lysis reaction to complete in the reservoir 74b. The incubation time is controlled by two parameters: volume and viscosity of the first liquid introduced via reservoir 74a. As previously described above, when the liquid is fully drained into the absorption body 75, the liquid introduced into reservoir 74b begins to flow downstream of the lateral capillary matrix 73, and the DNA therein is captured by the capture zone 76a, which zone is characterized by high DNA binding capacity. It is to be noted that in this type of reaction, the capture zone is the entire, interior capture matrix. As the second solution fully drains into the absorbent body 75, the third solution in reservoir 74c washes the capture zone 76a of non-DNA materials. The capturing matrix 76 is then removed from the device, transferred by tube contents DNA releasing solution (low salts solution), and then removed from the tube which contains free extracted DNA.

Different types of substance or molecules may be captured or extracted in the above-described method and device, including: Genomic DNA, plasmid DNA, mitochondrial DNA, and also mRNA. The extracted substance or molecules may be of different origins, blood, urine or any tissue from either human or animal, and may be used for diagnosis and analysis of bio-molecules. The embodiment illustrated in FIGS. 8 and 8a is particularly useful for nucleic acid or protein modification that involves multi-step reactions. A typical modification is labeling of DNA or proteins with biotin. The labeling process can be performed as described above.

The FIGS. 9-12 Embodiments

Figure 9:
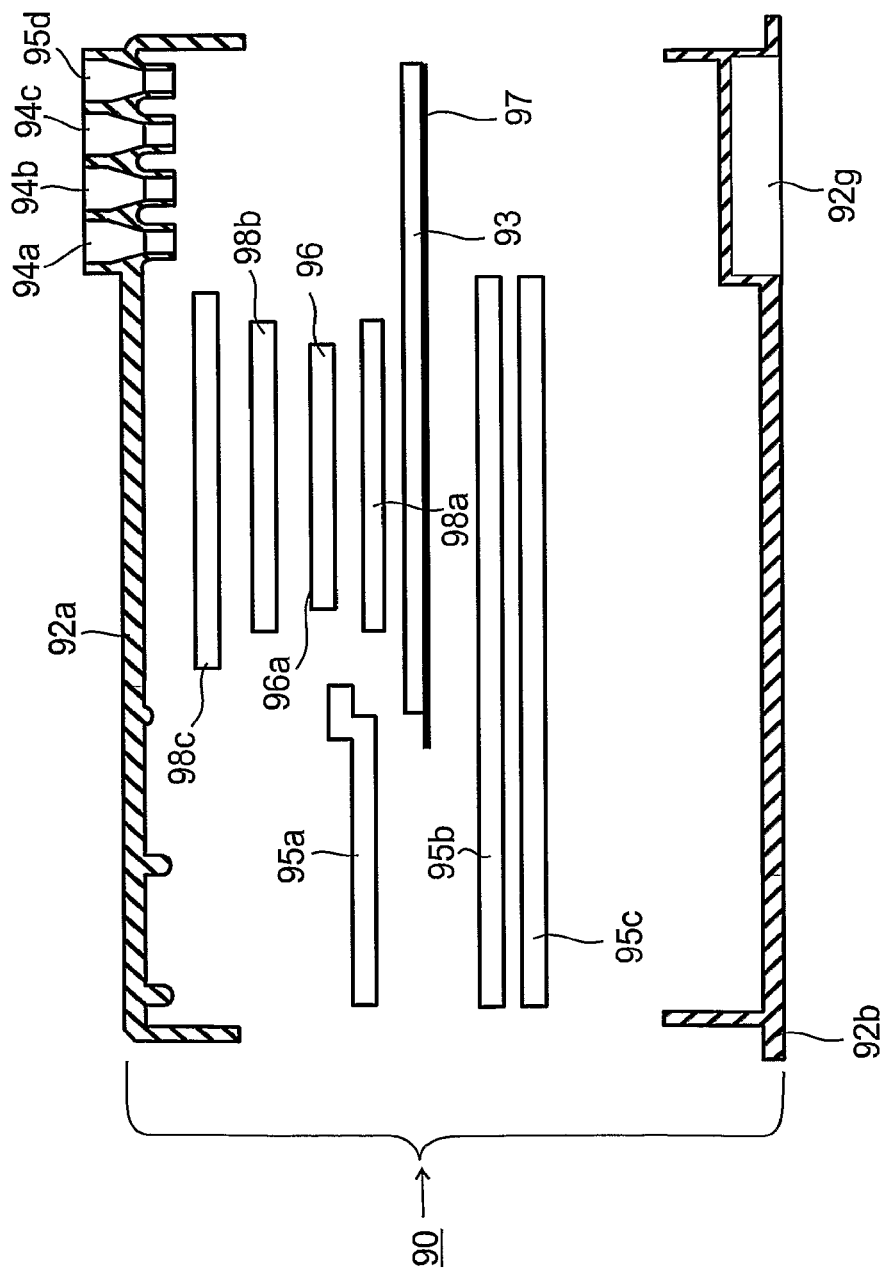
FIG. 9 illustrates a still further capillary flow device constructed in accordance with the invention.
Figure 10:
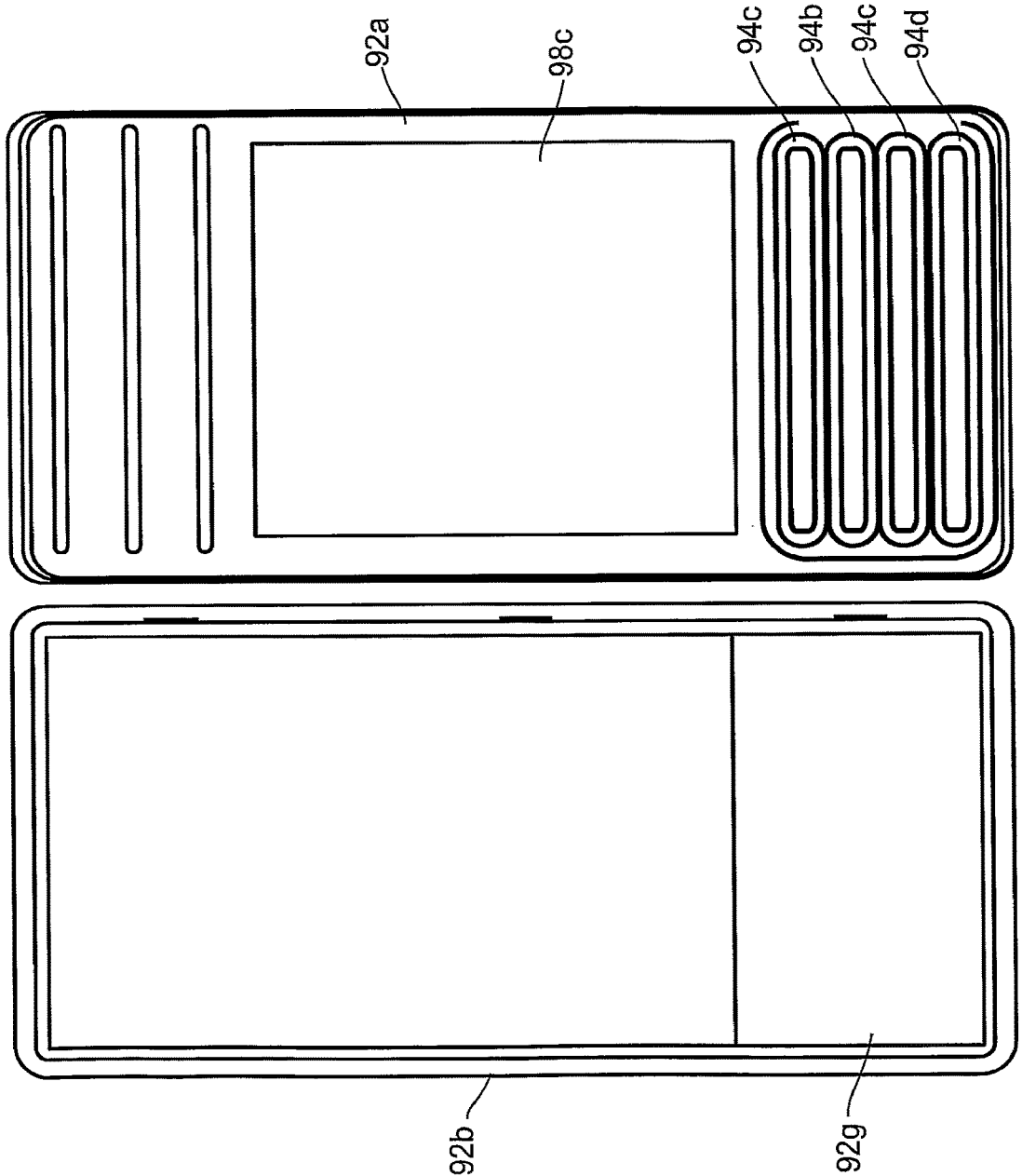
FIGS. 10A and 10B are bottom and top views, respectively, of the capillary flow device of FIG. 9 in its assembled condition.

FIG. 9 is an exploded view of still another capturing device, generally designated 90, which is of similar construction as that in FIG. 8, except for the following. Thus, in the device of FIG. 9, its top wall 92a is formed with four inlets 94a-94d, rather than three in FIG. 8, for introducing four liquids containing substances to be captured. In addition, the capturing matrix 96 in FIG. 9 is separated from the lateral capillary flow matrix 93 by an intermediate liquid-transfer matrix 98a, preferably in the form of a membrane, similar to intermediate liquid-transfer matrix 88 in FIG. 8. In addition, the upper side of capturing matrix 96 is contacted by another intermediate liquid-transfer matrix 98b and carrier matrix 98c, such that capturing matrix 96 is sandwiched between the two membranes 98a and 98b. Carrier matrix 98c has two purposes: to create parallel lateral flow to the lateral flow of the capillary flow matrix by direct contact with the lateral capillary flow matrix; and to prevent evaporation from the upper side of the capture matrix.

For purposes of example, the absorbent body in the device of FIG. 9 is in the form a plurality of sections 95a, 95b, 95c sandwiching the downstream end of the lateral capillary flow matrix 93, in the same manner as described above with respect to FIGS. 6a and 6b. The upstream end of the lateral capillary flow matrix 93, including its underlying plastic layer 97, is firmly clamped between the inwardly-extending step 92g in the housing bottom wall 92b and the lower rims of the liquid inlets 94a-94d.

During use of the disclosed device, the liquids are applied simultaneously or almost simultaneously to the inlets 94a-94d and reach the capture zone 96a of the capturing matrix 96 sequentially as described above with respect to FIGS. 8 and 8a. In substantially all other respects, the device illustrated in FIG. 9 is constructed, and operates, in the same manner as described above with respect to FIGS. 8 and 8a.

FIGS. 10a and 10b are bottom and top views, respectively, of the capturing device 90 illustrated in FIG. 9. As seen in FIG. 10a, and also in FIG. 9, the bottom housing wall 92b is formed with an inwardly-extending step 92g which is effective to press the lateral capillary flow matrix 93 firmly against the inner rims of the inlets 94a-94d. FIG. 10b also clearly shows the elongated configuration of the inlets 94a-94d so as to enable each inlet to serve as a reservoir for the liquid introduced therein.

Figure 11:
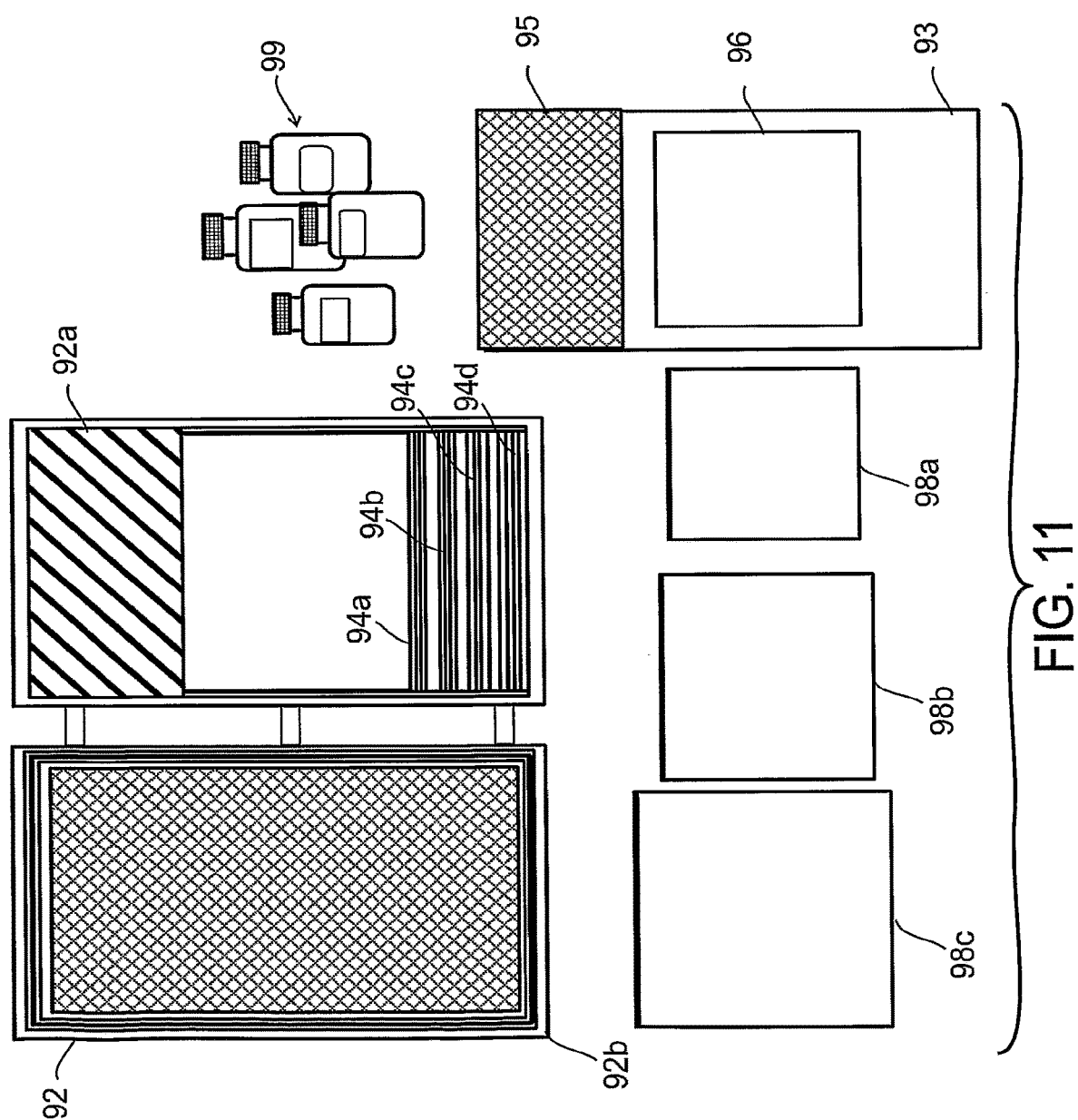
FIG. 11 illustrated the contents of a kit for use in making the capillary flow device of FIGS. 9-10B.

FIG. 11 illustrates a test kit that may be supplied for using any of the foregoing capturing devices, e.g. the device of FIG. 9. Such a test kit includes a plastic housing 92 including a top part 92a formed with the four inlets 94a-94d, at a bottom part 92b attachable to the top part. Also illustrated in FIG. 11 are the lateral capillary flow matrix 93, the absorbent body 95, the capturing matrix 96, the intermediate liquid-transfer matrix 98a separating the capturing membrane 96 from the lateral capillary flow matrix 93, and another intermediate liquid-transfer matrix 98b overlying the upper surface of the capturing membrane 96 and carrier membrane 98c. The kit would also include the various development liquids, generally shown at 99, for introduction into the capturing device as described above.

Figure 12:
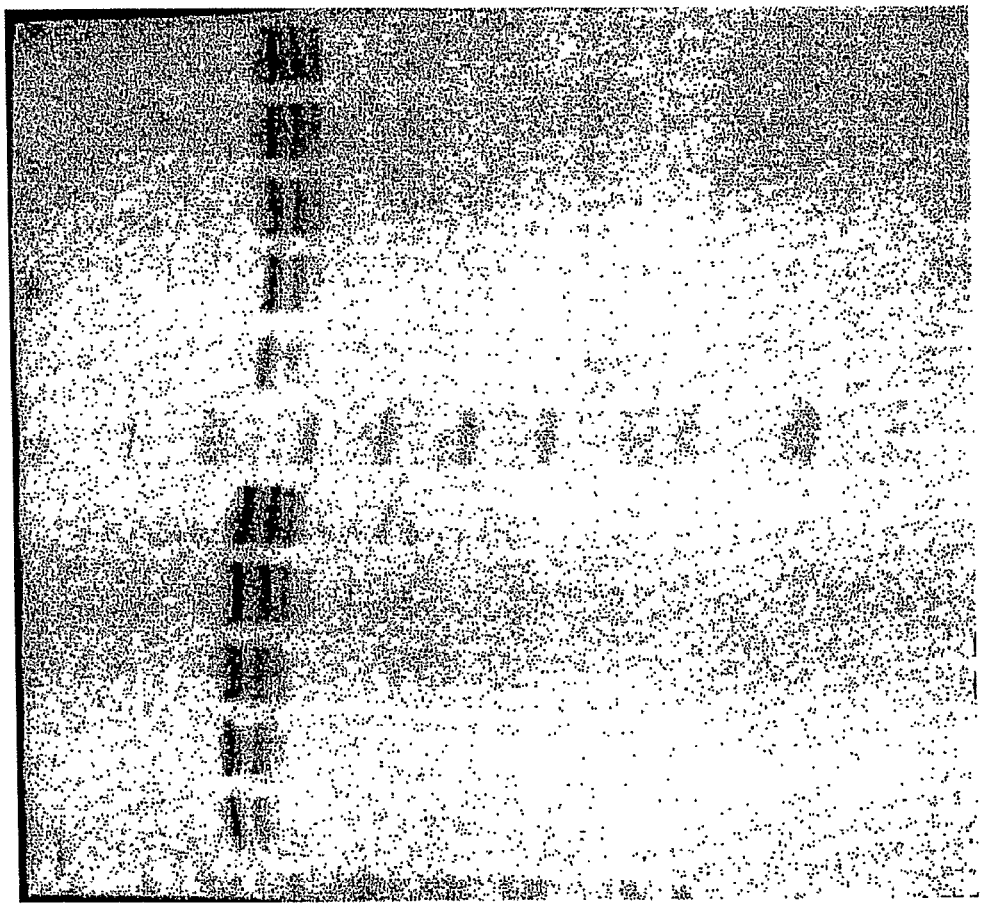
FIG. 12 illustrates an example of the results obtainable by the use of the capillary flow device of FIGS. 9-11B.

It will be appreciated that the devices described above may be used for different types of multi-step procedures, such as Nucleic Acid (NA) and protein blot membrane development, NA and protein modification, which modifications may be of the following types: tagging, cleavage, synthesis, coupling, and the like. FIG. 12 illustrates an example of western blot development results produced by using the above-described devices.

Figure 13:
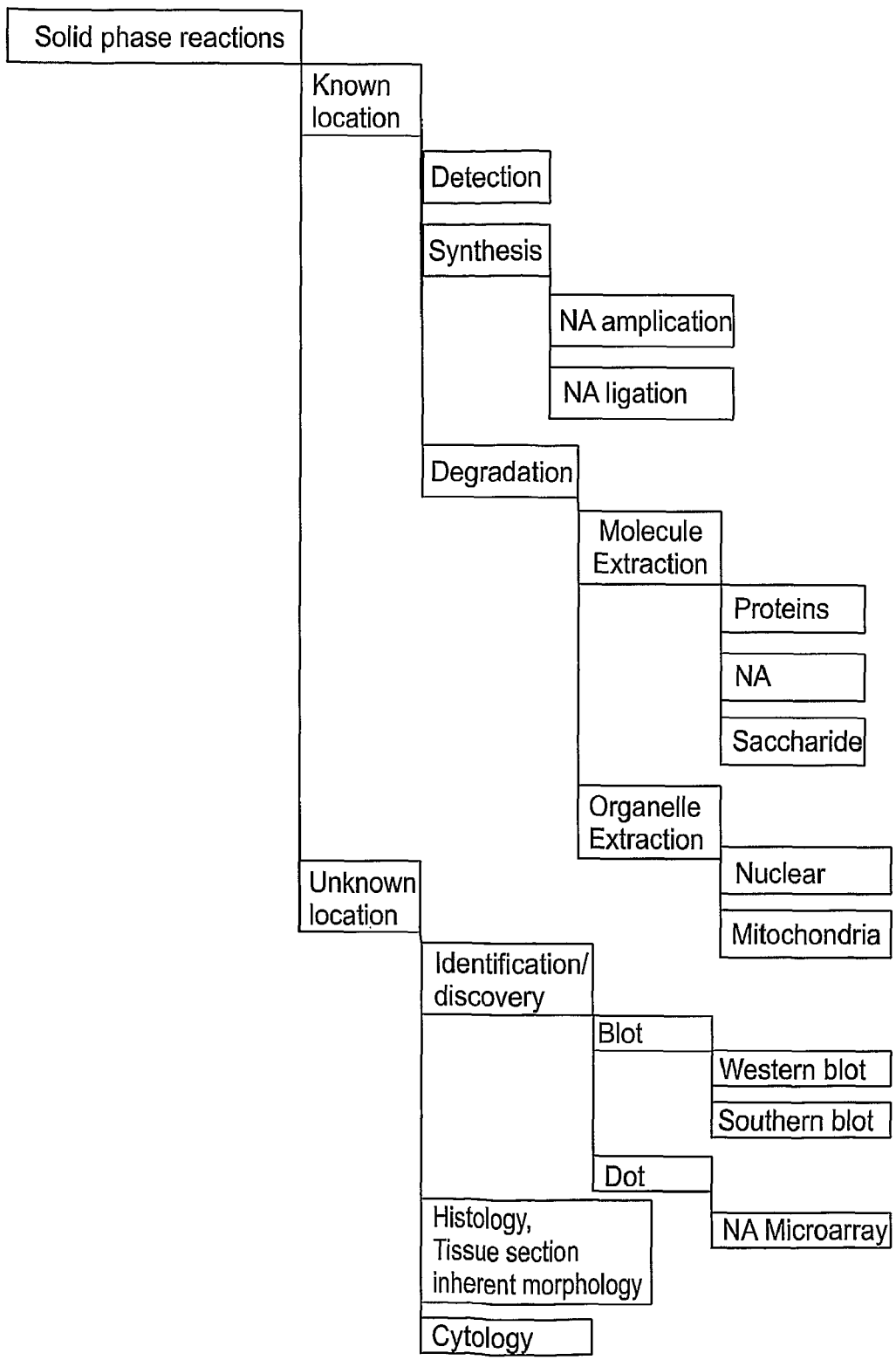
FIG. 13 is a flow chart illustrating solid phase reactions with respect to which the invention is particularly useful.

Description of Flowchart of FIG. 13

As indicated earlier, the flowchart of FIG. 13 illustrates various types of solid phase reactions with respect to which the present invention is particularly useful.

The flowchart shows that essentially two different types of solid phase reactions are envisaged by the present inventors. The first type of reaction is where the substrate is localized to a known position on the capturing matrix.

The biological substrate in this case is typically a molecule (e.g. a polypeptide, a polynucleotide, a carbohydrate) a complex (such as a protein complex) or a cell.

In one embodiment, a capturing molecule is localized to a known position on the capturing matrix (e.g. an antibody is placed at a known position on the capturing matrix). The capturing molecules may be attached to the capturing zone using any method known in the art including but not limited to absorption, sequestration, aminosilane/carbodiimide coupling of nucleic acid to glass substrate etc.

Typical reactions that may be performed using this type of reaction include, immunodetection, synthesis of macromolecules including peptides and nucleic acids (e.g. siRNAs). In order to determine whether the substrate has bound to the capturing molecule, a detection reaction may be performed. Alternatively, the substrate itself may have a detectable moiety (e.g. a color, or a fluorescent moiety) such that capture of substrate may be confirmed without the need for an additional reaction.

In another embodiment, the substrate is localized directly to the capturing matrix without a capturing molecule intermediate. According to this embodiment, a biological substance may be isolated using the devices of the present invention by binding directly to the capturing zone (e.g. by virtue of having an affinity due to the charge or trapping by size in the capture zone).

Following capturing of a biological substance, the present inventors envisage that the captured substance may be retained on the capturing membrane in order to be detected or for further manipulation—e.g. biotinylation, addition of nucleotoides, removal of phosphates etc.

The second type of reaction is where the substrate is pre-localized the capturing matrix, but its position is unknown. The substrate for these types of reactions may be a molecule, an organelle (e.g. a nucleus or mitochondria), a particular cell type or even a tissue. The device of the present invention may be used to determine the localization of the substrate. Examples of this type of reaction include, but are not limited to Western blots, Southern blots, Northern Blots, immunoprecipitations, dot blots, microarrays etc. The device of the present invention may also be used to determine the localization of a particular molecule within the substrate. Thus the second type of reaction also includes histological reactions, whereby the capturing matrix is a slide and the substrate is a cell or tissue prelocalized on the slide. The device of the present invention may be used to perform analysis (e.g. immuohistochemical analysis) of the substrate.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Experiment 1: Preparation and Detection of Capillary Based Blot Development Device Utilizing Single Reservoir The assay device is depicted in FIGS. 5a and 6a.

Capturing Matrix Preparation:

Capturing zone preparation: 10 µl, 4 µl, 2 µl, 0.5 µl/lane of MagicMark™ XP Western Protein Standard (IgG binding site recombinant) (Invitrogen Inc.) were loaded onto an Acrylamide gel and separated by electrophoresis. The proteins were transferred onto 0.2 µm Nitrocellulose membrane (70 mm×70 mm) thus creating the capturing zone (CZ) side of the capturing matrix. The membrane was immersed into blocking solution (1% BSA in PBS) for 30 min at RT before assembling into the assay device.

Capillary Flow Unit Preparation:

Preparation of capillary flow unipath: A glass fiber porous membrane was used as the lateral capillary flow matrix. It was cut into a sheet having 125 mm length and 90 mm width. A supporting layer such as LH-50 (Advanced Microdevices Pvt. Ltd.), a HIPS plastic with adhesive and typical dimensions of 0.5 mm thickness was cut into the same dimensions of 130 mm length and 90 mm width. The capillary flow matrix was attached to a plastic supporting layer in such a way that it covered the almost entire plastic supporting layer exposed 5 mm in the distal end.

Preparation of absorbent: The absorbent was cellulose chromatograph paper Chr 17 (Whatman). It was cut into three portions of the following dimensions: First portion of 90 mm width and 50 mm, length; and two identical portions of 90 mm width and 130 mm length.

The first portion (90 mm×50 mm) was attached at the distal end of the capillary flow unipath.

The two identical portions (90 mm×130 mm) were added to the lower part of the housing device beneath the attached first absorbent portion to the capillary flow unipath.

Assembly of Liquid-Transfer, or Capturing, Matrix in the Assay Device:

The capturing matrix was placed on the top of the capillary flow unit so that the capturing matrix and the lateral capillary flow matrix were in full contact. During the placement of the capturing matrix on the lateral capillary flow matrix one has to avoid trapping of air bubbles between the two matrices. The upper part of the housing device was closed against the lower part.

Operation of the Assay Device:

Development solutions from Westembreeze—Chromogenic Western Blot Immunodetection kit (Invitrogen inc.) were applied to the reservoir in the following order: first, 2 ml of 1% BSA in PBS solution is applied to reservoir.

After liquid drained, a second solution of 2 ml of the alkaline phosphatase conjugate ab (2nd ab) was applied to the reservoir and allowed to drain off. Upon complete draining of the solution, 3 ml of the substrate solution (BCIP/NBT) was applied to the reservoir, and finally after complete draining of the third solution, a forth liquid of 3 ml DDW was applied to the reservoir in order to stop the color reaction. To visualize the developed bands the device was opened and the capturing matrix was removed and dried. Nine distinct bands ranging from 20 to 220 kda appeared at the end of development.

Experiment 2: Preparation and Detection of Capillary Based Blot Development Device Utilizing a Capturing Membrane Beneath the Lateral Capillary Flow Matrix The assay device is depicted in FIGS. 5a and 6a.
Liquid-Transfer, or, Capturing, Matrix Preparation:
Capturing zone preparation: 2 μl, 0.5 μl, 0.25 μl/lane of SW480 Human colon cancer cell lysate were loaded and separated on Acrylamide gel electrophoresis. The lysate proteins were transferred into 0.45μ PVDF membrane (70 mm×70 mm) creating the capturing zone side of the capturing matrix. The blotted membrane was activated in methanol and immersed into blocking solution (1% BSA in PBS) for 30 min at RT before assembling into the assay device.

Capillary Flow Unit Preparation:
Preparation of capillary flow unipath: A glass fiber porous membrane was used as the lateral capillary flow matrix. It was cut into a sheet having 125 mm length and 90 mm width. A supporting layer of LH-50 (Advanced Microdevices Pvt. Ltd.; a HIPS plastic with adhesive and typical dimensions of 0.5 mm thickness) was cut into 130 min length and 90 mm width. The lateral capillary flow matrix was attached to a plastic supporting layer at its lower part in typical dimension of 40 mm×90 mm of the end.

Preparation of absorbent: The absorbent, which was cellulose chromatograph paper Chr 17 (Whatman), was cut into three portions, the first absorbent portion had dimensions of 90 mm width and 50 mm in length, and two identical portions of 90 mm width and 130 mm in length.

The two identical portions (90 mm×130 mm) were placed in the lower part of the housing device.

Assay Device Assembly:
The capturing matrix was attached to the capillary flow unipath in the middle part of the plastic supporting layer adjacent to the attached part of the lateral capillary flow matrix in such manner that the capture zone side of the capturing matrix was in full contact with the lateral capillary flow matrix and the capturing matrix was covered by the lateral capillary flow matrix. The capillary flow unipath attached to the capturing matrix was placed in the lower part of the device as depicted in FIG. 6b and the first portion of the absorbent was attached at the distal end of the capillary flow unipath. The upper part of the housing device was closed against the lower part—FIG. 6b.

Operation of the Assay Device:
Development solutions from Westembreeze—Chromogenic Western Blot Immunodetection kit (Invitrogen inc.) were applied to the reservoir, in the following order: 2 ml of the mixed primary Abs (Anti tubulin; Anti actin) solution. After liquid was drained, 2 ml of the secondary alkaline phosphatase conjugate Ab was applied. After liquid was drained, 3 ml of the substrate solution (BCIP/NBT) was applied and finally after liquid was drained completely from the reservoir, 1.5 ml of DDW was applied in order to stop the color reaction. For visualizing or reading the results, the device was opened and the capturing zone matrix removed and dried. Two distinct bands appeared at the end of development.

Experiment 3: Capillary Flow Unipath Device Having Several Reservoirs

The assay device is described in FIG. 7.
Liquid-Transfer, Or, Capturing, Matrix Preparation
Capture zone preparation: a strip of Nitrocellulose, PRIMA 85 (Schleicher & Schuell USA) was used. The capture zone was shaped as dots at the middle of the capturing matrix. The capture antibody solution was prepared as a mixture of, 0.1 mg/ml Rabbit anti calf Alkaline Phosphates (Biogenesis 0300-1024) and 0.4 mg/ml Rabbit IgG I 5006 (Sigma-Aldrich) in 0.1 M phosphate buffer (pH 6.8) and 2% Trehalose solution. One microliter of the solution was applied on the capture zone and dried at 37° C. for 15 minutes, then immersed for a few minutes in solution of 0.5% gelatin, 2.5% Bacto-Tryptone, 1% trehalose in PBS and dried at 37° C. for at least 2 hours.

Capillary Flow Unit Preparation:
Preparation of capillary flow unipath: A porous membrane of glass fiber was used as the lateral capillary flow matrix, cut into strips. A supporting layer of LH-50 (Advanced Microdevices Pvt. Ltd.; a HIPS plastic with adhesive and typical dimensions of 0.5 mm thickness) was cut into a strip. The lateral capillary flow matrix was attached to a plastic supporting layer in such way that the lateral capillary flow matrix covered the entire plastic supporting layer, except for 5 mm at the distal end which was exposed for attaching to one of the absorbents.

Preparation of absorbent: The absorbent was cellulose chromatograph paper Chr 17 (Whatman) cut into two portions strips.

One portion of absorbent was added to the lower part of the housing device beneath the capillary flow unipath attached to the absorbent.

Assembly of liquid-transfer, or capturing, matrix in the assay device:
The capturing matrix was positioned on the top of the lateral capillary flow matrix downstream to the liquid receiving zone so that the applied antibodies side of the capture zone was in full contact with the lateral capillary flow matrix. The upper part of the housing device was closed against the lower part.

Preparation Development Solutions:
Solution A: Alkaline Phosphatase—50 ul Alkaline Phosphatase (Boehringer Mannheim, Inc.) diluted in 1% BSA, 0.05% Tween-20, 0.1 mM $ZnCl_2$, 1 mM $MgCl_2$ in PBS buffer PH 7.4.

Solution B: AP substrate—BCIP/NBT was prepared according to Manufacturer instruction: Stock preparation—1 tablet BCIP, B0274 (Sigma-Aldrich) dissolved in 1 ml DMF, 1 tablet NBT, N55141 (Sigma-Aldrich) dissolved in 1 ml water. 33 μl of BCIP and 333 μl NBT from the stock solutions were added into 10 ml 0.1 M Tris buffer pH 9.7.

Solution C: Stop solution—0.25 M sulfuric acid
Operation of the Assay Device:
The one step operation was initiated by simultaneous application of development solutions A, B, C to the three reservoirs. 150 μl of solution A was added to the first reservoir, 300 μl of solution B was added to the second reservoir and 120 μl of solution C was added to the third reservoir. The reactions proceed automatically until the solutions were soaked up completely by the absorbent. Upon application of the solutions to the reservoirs, they immediately migrated into the lateral capillary flow matrix creating two liquid-liquid boundaries in the lateral capillary flow matrix—one boundary was created between solution A and solution B and the other between solution B and solution C. Solution A from the first reservoir flows from the reservoir toward the absorbent and contacted the capturing zone of the capturing matrix. The reagent solution B in the second reservoir started to drain only after solution A was completely drained out from the first reservoir. Solution C started to flow as solution B was completely drained off from the second reservoir. Colored dot signal were developed on the capture zone during the flow of solution and was terminated by the flow of solution C.

To analyze the results, the device was opened and the capturing matrix was removed, dried and visualized.

Experiment 4: Preparation of Diagnostic Device and Performing HIV-1 Test

A blood serum sample was tested in an assay device prepared as described in Example 3, except that the capture zone of the capturing matrix was prepared by applying two test lines. The first line was prepared by applying a line of drops (1 µl each) of 0.7 mg/mL HIV-1 recombinant protein antigen HIV-101 (ProSpec-Tany TechnoGene LTD) in 0.1 M phosphate buffer (pH 6.8) and 2% trehalose solution and the second line was prepared by applying drops (1 µl each) of a mixture of 0.1 mg/ml Rabbit anti calf Alkaline Phosphates (Biogenesis 0300-1024) and 0.4 mg/ml Rabbit IgG I 5006 (Sigma-Aldrich) in 0.1 M phosphate buffer (pH 6.8) and 2% Trehalose solution.

Preparation of the Liquids Precipitated in the Reaction (LPIR):

Solution A, Biotinylated synthetic gp41 and gp120 peptides diluted in BSA buffer. Solution B, Streptavidin-Alkaline Phosphatase conjugate (Jackson ImmuonResearch laboratories Inc.) diluted in 1% BSA, 0.5% tween-20, 0.1 mM $ZnCl_2$, 1 mM $MgCl_2$ in PBS buffer pH 7.4, Solution C, BCIP/NBT substrate.

Operation of the Assay:

Sample and the LPIRs were applied almost simultaneously to their corresponding reservoirs. 50 µl serum sample and 50 µl of solution A were added to the first reservoir, 50 µl of solution B was added to the second reservoir and 150 µl solution C was added to the third reservoir. The liquids migrated and the assay was completed when solution C was exhausted from the third reservoir. Presence of signals on both capture zone lines indicated the presence of antibodies for HIV-1 in the serum sample.

Experiment 5: Preparation and Detection of Blot Membrane Development Utilize Multiple Reservoirs Device and Membranes Set The assay device is depicted in FIG. 9.

Liquid-Transfer, or Capturing, Matrix Preparation:

0.5 µg, 0.25 µg, 0.125 µg, 0.062 µg, 0.031 µg/lane of SW480 Human colon cancer cell lysate were loaded in duplicates and separated on Acrylamid gel electrophoresis. The gel separated proteins (lanes 2-6 and 8-12 respectively) were transferred into 0.2 µNC membrane (70 mm×70 mm) creating the capture zone.

Capillary Flow Unit Preparation:

Preparation of absorbent: The absorbent, a cellulose chromatograph paper Chr 17 (Whatman) was cut into 3 portions, two identical absorbent sheets of 88 mm width and 118 mm length and one absorbent sheets of 88 mm width and 42 mm length.

Preparation of capillary flow unipath: The lateral capillary flow matrix, a porous membrane of glass fiber was cut into a sheet having 125 mm length and 88 mm width. A supporting layer of LH-50 (Advanced Microdevices Pvt. Ltd.) having 130 mm length and 88 mm width was attached to the lateral capillary flow matrix. The plastic supporting layer was covered entirely by the porous membrane except 5 mm in length at the distal end to which the absorbent sheet portion (88 mm width and 42 mm length) was attached.

Preparation of the Membrane Set:

Glass fiber membrane cut into piece with dimensions of 85 mm width and 75 mm length was used to create the carrier membrane.

Polyethylene (PE) membrane 0.010" (Porex Corporation) was cut into two identical pieces with dimensions of 72 mm width and 72 mm length to create the intermediate membranes.

Assay Device Assembly and Operation:

The two identical absorbent sheets (88 mm×130 mm) and the capillary flow unipath attached to absorbent were placed in the lower part of the housing device, Pre-Wetting Step:

3 ml of diluent solution (1% BSA, 0.05% tween-20 in PBS) was applied to the middle lower part of the porous membrane of the capillary flow unipath.

5 ml of diluent solution was applied onto a clean dish first, the intermediate membrane was immersed into the diluent solution and placed in full contact above the lateral capillary flow matrix 5 mm from the absorbent Then, the capturing matrix (blot membrane) was immersed into the diluent solution and placed in full contact, in the middle of the intermediate membrane. Then the second intermediate membrane was immersed into the diluent solution and placed in full contact above the blot membrane. The carrier membrane was wet and placed in full contact above the intermediate membrane and in direct contact with lateral capillary flow matrix.

The upper part of the housing device was closed against the lower part and the device was ready for performing the assay.

4 solutions were add simultaneously to the four reservoirs 94a, 94b, 94c and 94d, 2 ml of diluent solution (1% BSA, 0.05% Tween-20 in PBS) was applied to reservoir 94a, 2 ml of the primary antibody, mouse anti B catenin in diluent solution, was applied to reservoir 94b, 2 ml of the secondary antibody solution, goat anti mouse alkaline phosphatase conjugate in diluent solution, was applied to reservoir 94c and 7 ml diluent solution was applied to reservoir 94d. The reactions proceeded automatically until the solutions were completely soaked. To analyze the results, the device was opened and the capture matrix was immersed into 5 ml of chromogenic substrate (BCIP/NBT) for 15 minutes, then transferred to 20 ml of distilled water for 2 minutes and dried on a clean piece of filter paper. The bands were visualized. (FIG. 12).

Example 6: Capillary Flow Unipath Device for Performing a Microarray Slide Assay The assay device is described in FIG. 8a accept that it has 4 inlets.

Liquid-Transfer, or Capturing, Matrix Preparation:

A silanized glass microscope slide was used as the capturing matrix. The capture zone was prepared by printing peptide antigens and controls on a silanized microscope glass slide.

Samples were transferred from microtiter plates 384 wells, to the capturing matrix by use of stainless steel solid pins (200-µm diameter). Each pin was estimated to transfer ~1 nl of antigen solution to the slide. The capturing matrix included a matrix of antigens, controls like human IgG and IgM internal calibration curves and labeled anti human IgG Cy5 and anti human IgM Cy3 reference for the signals intensity. Antigens were dissolved in PBS containing Tween 20 (0.1 mL/L). Polyvinylpyrrolidone (PVP) (10 g/L) was added to the human IgG, Sodium Dodecyl Sulfate (0.1 g/L) was added to the human IgM solution. Printing was performed in a chamber at 25° C. and 55% humidity. Printed slides were incubated for 12 hours inside the chamber before being assembled into the device.

Capillary Flow Unit Preparation:

Preparation of capillary flow unipath: A porous membrane of glass fiber was used as the lateral capillary flow matrix, cut into strips having 130 mm length and 30 mm width. A supporting layer of LH-50 (Advanced Microdevices Pvt. Ltd.; a HIPS plastic with adhesive and typical dimensions of 0.5 mm thickness) was cut into a strip having the same dimensions as the lateral capillary flow matrix. The lateral capillary flow matrix was attached to a plastic supporting layer.

Preparation of absorbent: The absorbent of cellulose chromatograph paper Chr 17 (Whatman) was cut into 2 portions in the shape of strip, 30 mm width.

Assembly of the Assay Device:

The second portion of the absorbent, the capillary flow unipath and the first portion of absorbent were placed in the lower part of the hosing device.

The intermediate membrane was positioned in full contact on the top of the lateral capillary flow matrix downstream to the liquid receiving zone. The capturing matrix was placed on the top of the intermediate membrane so that the applied antibody side of the capturing matrix is in full contact with the intermediate membrane. The upper part of the housing device was closed against the lower part.

Operation of the Assay Device:

Sample solution and the LPIRs were applied almost simultaneously to their corresponding reservoirs 74a-74d. 200 µl of blocking solution 1% BSA in PBS was applied to reservoir 74a 200 µl of the sample solution, human serum sample diluted 1:200 in 1% BSA PBST (PBS and Tween20) was applied to reservoir 74b, 200 µl of the LPIR solution, mix of cy5 anti-human IgG and cy3 anti-human IgM in 1% BSA PBST was applied to reservoir 74c and 600 ul of the PBST solution was applied to reservoir 74d. In sequential order, the blocker solution, the sample solution and the LPIR migrated through the lateral capillary flow matrix and the intermediate membrane towards the absorbent, reacting with the capture zone in the capturing matrix. The assay was completed when solution "d" was exhausted from reservoir 74d. The capturing matrix was then detached from the device, washed by dipping in DDW, dried at 37° C. and results were read by fluorescence scanner.

Example 7: Preparation and Use of Capillary Flow Unipath Device for DNA Extraction from Human Blood Sample For performing a sample extraction assay, the assay device described in FIG. 8a was used:

Liquid-Flow, or, Capturing Matrix Preparation:

A strip of activated silica membrane was used as capture matrix and served as the capture zone for capturing the genomic DNA.

Capillary Flow Unit Preparation:

The capillary flow unipath and absorbent were prepared as described in Example 3 except that the porous membrane used as the lateral capillary flow matrix was nitrocellulose 15 µm (MSI Inc.)

Assembly of Capturing Matrix in the Assay Device:

The assembly of the intermediate membrane and the capturing matrix in the device was performed as described in Example 6.

Preparation of Assay Solution:

Solution a—comprises lysis buffer and PVP; solution b—lysis buffer and proteinase k; solution c—wash solution comprises salt and detergent.

Operation of the Assay Device:

Solutions a, b, c and sample were added almost simultaneously to reservoirs 74a, 74b, and 74c. 200 µl of solution a were added to reservoir 74a, 150 µl of solution b and 50 µl of whole blood sample were added to reservoir 74b and 200 µl of solution c were added to reservoir 74c. The reactions proceed automatically until the solutions were completely soaked by the absorbent. The 3 solutions migrated into the lateral capillary flow matrix creating two liquid-liquid boundaries in the lateral capillary flow matrix, one boundary was created between solution a and solution b and the other between solution b and solution c. Solution a from reservoir 74a flowed from the reservoir and appeared in the capture zone in the capturing matrix. The solution b in reservoir (74b) started to drain only after solution a was completely drained out from the first reservoir; this allowed sufficient controlled incubation time for the activity of the lysis buffer and the Proteinase k. Solution c started to drain when solution b drain completely from reservoir (74b) washing away all unbound molecules ensuring complete removal of any residual contaminants from the capture zone. When solution c drained completely, the device was opened and the capturing matrix was transferred to a tube containing 100 µl nuclease-free DDW for eluting the captured DNA.

Experiment 8: Utilizing Multiple Reservoirs Device for Direct Gel Detection

The assay device is depicted in FIG. 9.

Liquid-Transfer, or Capture, Matrix Preparation:

2 µl, 0.5 µl, 0.25 µl/lane of SW480 Human colon cancer cell lysate were loaded and separated on Acrylamid gel electrophoresis. The separated proteins matrix created the capture zone.

Capillary Flow Unit Preparation:

Preparation of absorbent: The absorbent, cellulose chromatograph paper Chr 17 (Whatman) was cut into 3 portions, two identical absorbent sheets of 88 mm width and 118 mm length and one absorbent sheets of 88 mm width and 42 mm length.

Preparation of capillary flow unipath: A porous membrane of glass fiber was used as the lateral capillary flow matrix. It was cut into a sheet having 125 mm length and 88 mm width. A supporting layer such as LH-50 (Advanced Microdevices Pvt. Ltd.; a HIPS plastic with adhesive and typical dimensions of 0.5 mm thickness) was cut into 130 mm length and 88 mm width. The lateral capillary flow matrix was attached to the plastic supporting layer in such way that it almost covered the entire plastic supporting layer, except for 5 mm in length at the distal end in which the absorbent sheet portion (88 mm width and 42 mm length) was attached.

Preparation of the Membranes Set:

The glass fiber membrane was cut into piece with dimensions of 85 mm width and 75 mm length to create the carrier membrane.

Polyethylene (PE) membrane 0.010" (Porex Corporation) was cut into two pieces with dimensions of 72 mm width and 72 mm length to create the intermediate membranes.

Assay device assembly and operation:

The two identical absorbent sheets (88 mm×130 mm) and the capillary flow unipath were placed in the lower part of the housing device.

Pre-wetting step: 3 ml of diluent solution (1% BSA, 0.05% Tween-20 in PBS) was applied to the middle lower part of the porous membrane of the capillary flow unipath.

5 ml of diluent solution was applied onto a clean dish. First, the intermediate liquid-transfer membrane was immersed into the diluent solution and placed in full contact above the lateral capillary flow matrix, 5 mm from the absorbent. Then the capturing matrix was placed in full contact, in the middle of the intermediate liquid-transfer membrane, with the gel lanes being in parallel to the device length. Then the second liquid-transfer intermediate membrane was immersed into the diluent solution and placed in full contact above the gel. Eventually the carrier membrane was wet and placed in full contact above the liquid-transfer intermediate membrane and with direct contact with the lateral capillary flow matrix.

The upper part of the housing device was closed against the lower part and the device was ready for performing the assay.

Four solutions were added simultaneously to reservoirs 94a, 94b, 94c and 94d, 1.5 ml of the diluent solution was applied to reservoir 94a, 1.5 ml of the primary antibody mouse anti β-catenin solution was applied to reservoir 94b, 1.5 ml of the secondary antibody goat anti mouse conjugate was applied to reservoir 94c and 7 ml diluent solution was applied to reservoir 94d. The reactions proceeded automatically until the solutions were completely soaked. To analyze the results the device was opened and the gel was immersed into 10 ml of chemiluminescent substrate for 5 min at RT. Then the gel was exposed to X-ray film. The bands were visualized.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

While the invention has been described to several embodiments, it will be appreciated that these are set forth merely for purposes of example, and that many other variations, modifications and applications of the invention may be made.

What is claimed is:

1. An assembly comprising:
    a housing having a closed configuration defining an interior and comprising an inlet in flow communication with the interior and positioned to receive liquid from a source exterior to the housing;
    a lateral capillary flow matrix in the interior, the lateral capillary flow matrix positioned to receive the liquid from the inlet, the lateral capillary flow matrix made of a first material having a first wicking rate, the lateral capillary flow matrix comprising a surface region, the lateral capillary flow matrix defining a lateral capillary flow path extending from a first end to a second end of the lateral capillary flow matrix, and the first material of the lateral capillary flow matrix being configured to produce a lateral capillary flow of a liquid along the lateral capillary flow path in a first direction from the first end toward the second end;
    an absorbent material in the interior of the housing, the absorbent material contacting the second end of the lateral capillary flow matrix; and
    a liquid-transfer matrix in the interior, an entirety of a face of the liquid-transfer matrix in contact with the surface region of the lateral capillary flow matrix, the liquid-transfer matrix made of a second material having a second wicking rate less than the first wicking rate,
    wherein capillary passageways in each of the lateral capillary flow matrix and the liquid-transfer matrix are in fluid communication with each other, and
    wherein, in response to lateral capillary flow of liquid along the lateral capillary flow path of the lateral capillary flow matrix, the contact and the first and second wicking rates establish flow of liquid in the liquid-transfer matrix in a second direction transverse to the first direction.

2. The assembly of claim 1, wherein the absorbent material and the first material are a same material.

3. The assembly of claim 1, wherein the absorbent material and the lateral capillary flow matrix are formed integrally.

4. The assembly of claim 1, wherein the absorbent material and the lateral capillary flow matrix are discrete structures.

5. The assembly of claim 1, wherein the liquid-transfer matrix has a pore size, has a charge, or comprises a capture molecule enabling the liquid-transfer matrix to capture a biological substance from liquid flowing in the liquid-transfer matrix.

6. The assembly of claim 1, wherein the face of the liquid-transfer matrix is a first face and the assembly further comprises a capturing matrix in the interior in contact with a second face, opposite the first face, of the liquid-transfer matrix, the capturing matrix having a pore size, having a charge, or comprising a capturing molecule enabling the capturing matrix to capture a biological substance from liquid flowing in the liquid-transfer matrix.

7. The assembly of claim 6, wherein the capturing matrix comprises a plurality of capture zones sequentially spaced along a direction the capillary flow path extends, the plurality of capture zones comprising a capturing molecule enabling the plurality of capturing zones to capture a biological substance from liquid flowing in the liquid-transfer matrix.

8. The assembly of claim 6, wherein the liquid-transfer matrix is a first liquid-transfer matrix and the assembly further comprises a second liquid-transfer matrix in the interior, the capturing matrix being sandwiched between the first liquid-transfer matrix and the second liquid-transfer matrix.

9. The assembly of claim 8, further comprising a plastic layer in the interior underlying the lateral capillary flow matrix and positioned on an opposite side of the lateral capillary flow matrix from the liquid-transfer matrix.

10. The assembly of claim 9, wherein the absorbent material comprises:
   a first absorbent material membrane overlying a portion of the lateral capillary flow matrix proximate the second end and extending to a location downstream from the second end of the lateral capillary flow matrix, and
   a second absorbent material membrane underlying the plastic layer and extending from a location upstream of the first absorbent material membrane to the location downstream from the second end of the lateral capillary flow matrix.

11. The assembly of claim 10, wherein the absorbent material is cellulose chromatograph paper, the first liquid-transfer matrix and the second liquid-transfer matrix are made of polyethylene, and the lateral capillary flow matrix is made of glass fiber.

12. The assembly of claim 1, further comprising a plastic layer in the interior underlying the lateral capillary flow matrix and positioned on an opposite side of the lateral capillary flow matrix from the liquid-transfer matrix.

13. The assembly of claim 1, wherein the first material has a first pore size and the second material has a second pore size, the first pore size being larger than the second pore size.

14. The assembly of claim 13, wherein the first pore size is up to about 10 times larger than the second pore size.

15. The assembly of claim 13, wherein the first pore size ranges from about 1 micron to 15 microns, and the second pore size ranges from 0.1 micron to 5 microns.

16. The assembly of claim 1, wherein:
   the first end of the lateral capillary flow matrix is located proximate the inlet,
   the second end of the lateral capillary flow matrix is opposite the first end, and
   the lateral capillary flow path defined within the lateral capillary flow matrix extends continuously along a length of the lateral capillary flow matrix between the first end and the second end.

17. The assembly of claim 1, wherein the liquid-transfer matrix comprises a first affinity molecule having an affinity to capture a second affinity molecule, the first affinity molecule being retained in the liquid-transfer matrix so as to enable the liquid-transfer matrix to capture a biological substance from liquid flowing in the liquid-transfer matrix.

18. The assembly of claim 17, wherein one of the first affinity molecule and the second affinity molecule is an antigen, and the other of the first affinity molecule and the second affinity molecule is an antibody.

19. The assembly of claim 17, wherein one of the first affinity molecule and the second affinity molecule is a nucleic acid, and the other of the first affinity molecule and the second affinity molecule is a complementary nucleic acid.

20. The assembly of claim 17, wherein one of the first affinity molecule and the second affinity molecule is a ligand, and the other of the first affinity molecule and the second affinity molecule is a receptor.

21. The assembly of claim 1, wherein, in response to lateral capillary flow of liquid along the lateral capillary flow path of the lateral capillary flow matrix, the contact and the first and second wicking rates establish an oscillatory pattern of the flow of liquid in the liquid-transfer matrix in the second direction.

22. The assembly of claim 1, wherein the first material is a bibulous material.

23. The assembly of claim 7, wherein a capture zone of the plurality of capture zones comprises a first capturing molecule and another capture zone of the plurality of capture zones comprises a second capturing molecule different from the first capturing molecule.

24. The assembly of claim 1, wherein the housing comprises an upper portion and a lower portion.

25. The assembly of claim 24, wherein the upper and lower portions are configured for relative movement from the closed configuration of the housing to place the housing in an open configuration, and from the open configuration to place the housing in the closed configuration.

26. The assembly of claim 1, wherein the housing further comprises a window permitting observation of the interior in the closed configuration of the housing.

27. The assembly of claim 6, wherein the housing further comprises a window, the window positioned above the capturing matrix in the closed configuration of the housing.

28. The assembly of claim 24, wherein the upper portion comprises a top wall and the top wall comprises the inlet.

29. The assembly of claim 1, wherein, in the closed configuration of the housing, the inlet is above the lateral capillary flow matrix and the lateral capillary flow matrix is below the inlet to receive liquid inserted into the interior through the inlet.

30. The assembly of claim 1, wherein the assembly comprises a plurality of inlets, the plurality of inlets comprises the inlet, and each inlet of the plurality is positioned to receive liquid from a source exterior of the housing in the closed configuration of the housing, each inlet in flow communication with the interior.

31. The assembly of claim 30, wherein the plurality of inlets are sequentially arrayed from the first end toward the second end, and configured for introducing a plurality of liquids sequentially or simultaneously to the interior.

* * * * *